(12) United States Patent
Chern et al.

(10) Patent No.: US 6,995,306 B1
(45) Date of Patent: Feb. 7, 2006

(54) NUCLEIC ACID ENCODING AN NPR1 INTERACTOR FROM RICE AND METHOD OF USE TO PRODUCE PATHOGEN-RESISTANT PLANTS

(75) Inventors: Maw Shenq Chern, Davis, CA (US); Pamela Ronald, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/294,539

(22) Filed: Apr. 19, 1999

(51) Int. Cl.
*A01H 5/00* (2006.01)
*C12N 15/82* (2006.01)
*C12N 15/29* (2006.01)

(52) U.S. Cl. .................. 800/320.2; 800/279; 800/287; 800/301; 536/23.6

(58) Field of Classification Search ............... 536/23.6; 800/279, 301, 320.2, 287; 435/468, 418, 435/419
See application file for complete search history.

(56) References Cited

U.S. PATENT DOCUMENTS 5,986,082 A * 11/1999 Uknes et al. ............... 536/23.6
6,031,153 A * 2/2000 Ryals et al. ................. 800/279

FOREIGN PATENT DOCUMENTS

| WO | WO 98/06748 | * | 2/1998 |
| WO | WO 00/28036 A2 | | 5/2000 |
| WO | WO 00/70069 A1 | | 11/2000 |

OTHER PUBLICATIONS

Delaney, T. P. "New mutants provide clues into regulation of systemic acquired resistance." 2000, Trends Plant Sci., vol. 5, pp. 49-51.*
Cao, H. et al., "The Arabidopsis NPR1 Gene That Controls Systemic Acquired Resistance Encodes a Novel Protein Containing Ankyrin Repeats." 1997, Cell, vol. 88, pp. 57-62.*
Aguan, Kripamoy et al.; "Low-temperature-dependent expression of a rice gene encoding a protein with a leucine-zipper motif"; *Molecular and General Genetics*, vol. 240, No. 1, pp. 1-8.
Nakagawa, Hitoshi et al.; "A rice bZIP protein, designated OSBz8, is rapidly induced by abscisic acid"; 1996, *The Plant Journal.* vol. 9, No. 2, pp. 217-227.
Nakase, Masayuki et al.; "Characterization of a novel rice bZIP protein which binds to the α-globulin promoter"; 1997, *Plant Molecular Biology*, vol. 33, pp. 513-522.
Database NCBI, Dec. 13, 1999, Database accession No. AW231772, XP002273591.
Database NCBI, Mar. 28, 2000, Database accession No. AU086064, XP002273592.

* cited by examiner

Primary Examiner—Anne Kubelik
(74) Attorney, Agent, or Firm—Townsend and Townsend and Crew LLP

(57) ABSTRACT

The present invention provides the identification and characterization of a polynucleotide encoding rice PNI, a proline-rich protein that interacts with *Arabidopsis* NPR1 in a yeast two-hybrid assay. The present invention also provides methods of enhancing resistance to pathogens by introducing the polynucleotide[s] into plants.

21 Claims, No Drawings

NUCLEIC ACID ENCODING AN NPR1 INTERACTOR FROM RICE AND METHOD OF USE TO PRODUCE PATHOGEN-RESISTANT PLANTS

CROSS-REFERENCES TO RELATED APPLICATIONS

The application is related to the application U.S. patent application Ser. No. 09/267,031 filed on Mar. 11, 1999, now U.S. Pat. No. 6,137,031.

BACKGROUND OF THE INVENTION

Plant pathogens cause hundreds of millions of dollars in damage to crops in the United States annually and cause significantly more damage worldwide. Traditional plant breeding techniques have developed some plants that resist specific pathogens, but these techniques are limited to genetic transfer within breeding species and can be plagued with the difficulty of introducing non-agronomic traits that are linked to pathogen resistance. Furthermore, traditional breeding has focused on resistance to specific pathogens rather than general, or systemic, resistance to a wide spectrum of pathogens.

One of the most important crop plants in the world is rice. Little is currently known about the mechanisms by which rice resists pathogens. Therefore, an important goal in agriculture is to identify genetic components that enable plants in general, and rice in particular, to resist pathogens, thereby allowing for the development of systemically resistant plants through biotechnology.

Systemic acquired resistance (SAR) is a general plant resistance response that can be induced during a local infection by an avirulent pathogen. While early studies of SAR were conducted using tobacco mosaic virus (TMV) and its Solanaceous hosts (see, e.g., Ross, A. F. *Virology* 14: 340–358 (1961)), SAR has been demonstrated in many plant species and shown to be effective against not only viruses, but also bacterial and fungal pathogens (see, e.g., Kuc, J. *Bioscience* 32:854–860 (1982) and Ryals, et al. *Plant Cell* 8:1809–1819 (1996)). A necessary signal for SAR induction is salicylic acid (SA); plants that fail to accumulate SA due to the expression of an SA-oxidizing enzyme salicylate hydroxylase are impaired in SAR (Gaffney, T., et al. *Science* 261:754–756 (1993)). Conversely, an elevation in the endogenous level of SA or exogenous application of SA or its synthetic analogs, such as 2,6-dichloroisonicotinic acid (INA), not only results in an enhanced, broad-spectrum resistance but also stimulates concerted expression of a battery of genes known as pathogenesis-related (PR) genes (see, e.g., Malamy, J., et al. *Science* 250:1002–1004 (1990); Métraux, J.-P., et al. *Science* 250:1004–1006 (1990); Rasmussen, J. B., et al. *Plant Physiol* 97:1342–1347 (1991); Yalpani, N., et al. *Plant Cell* 3:809–818 (1991); White, R. F. *Virology* 99:410–412 (1979); Métraux, J.-P., et al. (1991) In *Advances in Molecular Genetics of Plant-Microbe Interactions*, eds. Hennecke, H. & Verma, D. P. S. (Kluwer Academic, Dordrechet, The Netherlands), Vol. 1, pp. 432–439; Ward et al. *Plant Cell* 3:1085–1094 (1991); and Uknes et al. *Plant Cell* 4:645–656 (1992)). PR genes may play direct roles in conferring resistance because their expression coincides with the onset of SAR and some of the PR genes encode enzymes with antimicrobial activities (see, e.g., Ward et al. *Plant Cell* 3:1085–1094 (1991); and Uknes et al. *Plant Cell* 4:645–656 (1992)). Therefore, understanding the regulation of PR gene expression has been a focal point of research in plant disease resistance.

The *Arabidopsis* gene NPR1 (Cao et al., *Plant Cell* 88(1):57–63 (1997) has been shown to be a key component of SA-regulated PR gene expression and disease resistance because npr1 mutants fail to express PR1, PR2, and PR5 and display enhanced susceptibility to infection even after treatment with SA or INA. Furthermore, transgenic plants overexpressing NPR1 display a more dramatic induction of PR genes during an infection and show complete resistance to *Pseudomonas syringae* pv. *maculicola* 4326 and *Peronospora parasitica* Noco, two very different pathogens that are virulent on wild-type *A. thaliana* plants (Cao, H., et al. *Proc. Natl. Acad. Sci. USA* 95:6531–6536 (1998)).

NPR1 contains at least four ankyrin repeats, which are found in proteins with very diverse biological functions and are involved in protein—protein interactions (Bork, P. (1993) *Proteins: Structure, Function, and Genetics* 17, 363–374. Michaely, P., and Bennet, V. (1992) *Trends in Cell Biology* 2:127–129.). The functional importance of the ankyrin repeat domain has been demonstrated by mutations found in the npr1-1 and the nim1-2 alleles where the highly conserved histidine residues in the third and the second ankyrin repeats, respectively, are changed to a tyrosine. Because these conserved histidine residues are involved in the formation of hydrogen bonds which are crucial in stabilizing the three dimensional structure of the ankyrin-repeat domain (Gorina, S. & Pavletich, N. P. *Science* 274, 1001–1005 (1996)), npr1-1 and nim1-2 mutations may cause disruption in the local structure within the ankyrin-repeat domain and abolish its ability to interact with other proteins. These data suggest that NPR1 may exert its regulatory function by interacting with other proteins.

bZIP proteins are one class of proteins that interact with NPR1 in a yeast two-hybrid system. bZIP proteins are transcription factors that have highly conserved DNA binding domains. Although functions have been postulated for some plant bZIP gene products (see, e.g., Kawata, T., et al. *Nucleic Acids Res.* 20, 1141 (1992); Xiang, C., et al. *Plant Mol. Biol.* 34, 403–415 (1997); Zhang, B., et al. *Plant J.* 4, 711–716 (1993); Schindler, U., et al., A. R. *Plant Cell* 4, 1309–1319 (1992); Miao, Z. H., et al. *Plant Mol. Biol.* 25, 1–11 (1994); and Lam, E. & Lam, Y. K.-P. *Nucleic Acids Res.* 23, 3778–3785 (1995); Foley et al., *Plant J.* 3(5): 669–79 (1993); Fromm, et al, *Mol. Gen. Genet.* 229:181–88 (1991); 1998 review, Schwechheimer and Bevan, *Trends in Plant Science,* 3:378 (1998); and Katagiri et al., *Nature* 340:727–30 (1989)), little is known about the regulation of bZIP gene products and there are no reports of their interaction with proteins associated with plant disease resistance, other than NPR1.

In spite of recent research of the genetic control of plant resistance to pathogens, little progress has been reported in the identification and analysis of gene products interacting with key regulators of pathogen resistance such as NPR1. Furthermore, most research has been carried out in model plant systems such as *Arabidopsis*. Little research has been performed on crop plants such as rice. Identification and characterization of rice NPR1 orthologs as well as rice gene products that interact with NPR1 or bZIP gene products would allow for the genetic engineering of plants with a variety of desirable traits. The present invention addresses these and other needs.

SUMMARY OF THE INVENTION

This invention relates to polynucleotides encoding PNI (proline-rich NPR1 interactor) polypeptides as well as polypeptides that interact with the polypeptides PNI or MN1, a rice bZIP protein that interacts with *Arabidopsis* NPR1. The invention also relates to transgenic plants containing such polynucleotides. The invention also relates to methods of enhancing resistance to pathogens in a plant by introducing the above-described polynucleotides into a plant and selecting for plants with enhanced resistance.

The present invention provides an isolated nucleic acid construct comprising a polynucleotide sequence that is at least 50% identical to a polynucleotide selected from the group comprising SEQ ID NO:1, SEQ ID NO:3, SEQ ID NO:5, SEQ ID NO:7, SEQ ID NO:9, SEQ ID NO:11, SEQ ID NO:13, SEQ ID NO:15, and SEQ ID NO:17; or encodes a polypeptide selected from the group comprising SEQ ID NO:2, SEQ ID NO:4, SEQ ID NO:6, SEQ ID NO:8, SEQ ID NO:10, SEQ ID NO:12, SEQ ID NO:14, SEQ ID NO:16, and SEQ ID NO:18. In one embodiment of the invention the polynucleotide is from a rice plant. In another embodiment, the construct further comprises a promoter operably linked to the polynucleotide sequence.

The invention also provides transgenic plants comprising a recombinant expression cassette comprising a plant promoter operably linked to a polynucleotide sequence that encodes a polypeptide wherein the polynucleotide: is at least 50% identical to a polynucleotide selected from the group comprising SEQ ID NO:1, SEQ ID NO:3, SEQ ID NO:5, SEQ ID NO:7, SEQ ID NO:9, SEQ ID NO:11, SEQ ID NO:13, SEQ ID NO:15, and SEQ ID NO:17; or encodes a polypeptide selected from the group comprising SEQ ID NO:2, SEQ ID NO:4, SEQ ID NO:6, SEQ ID NO:8, SEQ ID NO:10, SEQ ID NO:12, SEQ ID NO:14, SEQ ID NO:16, and SEQ ID NO:18. In one embodiment, the transgenic plant is rice.

The invention also provides a method of enhancing resistance to pathogens in a plant comprising two steps. One step involves introducing into the plant a recombinant expression cassette comprising a plant promoter operably linked to a polynucleotide sequence, wherein the polynucleotide sequence is at least 50% identical to a polynucleotide selected from the group comprising SEQ ID NO:1, SEQ ID NO:3, SEQ ID NO:5, SEQ ID NO:7, SEQ ID NO:9, SEQ ID NO:11, SEQ ID NO:13, SEQ ID NO:15, and SEQ ID NO:17; or encodes a polypeptide selected from the group comprising SEQ ID NO:2, SEQ ID NO:4, SEQ ID NO:6, SEQ ID NO:8, SEQ ID NO:10, SEQ ID NO:12, SEQ ID NO:14, SEQ ID NO:16, and SEQ ID NO:18. The second step involves selecting a plant with enhanced resistance.

Definitions

"Enhanced disease resistance" refers to an increase in the ability of a plant to prevent pathogen infection or pathogen-induced symptoms. Enhanced resistance can be increased resistance relative to a particular pathogen species or genus or can be increased resistance to all pathogens (e.g., systemic acquired resistance).

One of skill in the art will recognize that a polypeptide is "capable of interacting" with another polypeptide in a number of different ways. This interaction can, for instance, be a direct protein—protein interaction. Typical bonds formed in a protein—protein interaction include hydrogen, ionic, van der Waals and covalent bonds. Alternatively, the interaction may be indirect. For instance, a third polypeptide may bind to both polypeptides, thereby keeping all three polypeptides in proximity to one another. Protein interactions can be measured by a number of different methods that are known to those of ordinary skill in the art. Examples of systems to measure such interactions include, inter alia, the yeast two-hybrid system (see, e.g., Fields, *Nature* 340(6230):245–6 (1989) and Finley, R. L. JR & Brent R. (1996) in *DNA Cloning—Expression Systems: A Practical Approach*, eds. Glover D. & Hames B. D (Oxford University Press, Oxford, England), pp. 169–203), immunoprecipitation (see, e.g., Current Protocols in Molecular Biology Volumes 2, § 10.16, John Wiley & Sons, Inc. (1994–1998)), or the use of various sequence tags (e.g., TAG, His, etc.) that allow for the isolation of interacting polypeptides under nondenaturing conditions (see, e.g., Chen & Hai *Gene* 139(1):73–5 (1994); and Current Protocols in Molecular Biology Volumes 2, §§ 10.11A-B, 10.15, John Wiley & Sons, Inc. (1994–1998)). These methods can therefore be used to identify proteins that interact with polypeptides of the invention. One of ordinary skill in the art will recognize that protein—protein interactions can be measured by any number of methods and are not limited to those described above.

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A polynucleotide "exogenous to" an individual plant is a polynucleotide which is introduced into the plant by any means other than by a sexual cross. Examples of means by which this can be accomplished are described below, and include *Agrobacterium*-mediated transformation, biolistic methods, electroporation, and the like. Such a plant containing the exogenous nucleic acid is referred to here as a $T_1$ (e.g. in *Arabidopsis* by vacuum infiltration) or $R_0$ (for plants regenerated from transformed cells in vitro) generation transgenic plant. Transgenic plants that arise from sexual cross or by selfing are descendants of such a plant.

A "PNI" polypeptide of the invention is a subsequence or full length polypeptide sequence (SEQ ID NO:2) encoded by a polynucleotide (e.g., SEQ ID NO:1).

An "NH1" polypeptide of the invention is a subsequence or full length polypeptide sequence (SEQ ID NO:4) encoded by a polynucleotide (e.g., SEQ ID NO:3).

An "NH2" polypeptide of the invention is a subsequence or full length polypeptide sequence (SEQ ID NO:6) encoded by a polynucleotide (e.g., SEQ ID NO:5).

An "MN 1" polypeptide of the invention is a subsequence or full length polypeptide sequence (SEQ ID NO:20) encoded by a polynucleotide (e.g., SEQ ID NO:19).

In the case of both expression of transgenes and inhibition of endogenous genes (e.g., by antisense, or co-suppression) one of skill will recognize that the inserted polynucleotide sequence need not be identical, but may be only "substantially identical" to a sequence of the gene from which it was derived. As explained below, these substantially identical variants are specifically covered when references are made to a nucleic acid of the invention.

In the case where the inserted polynucleotide sequence is transcribed and translated to produce a functional polypeptide, one of skill will recognize that because of codon degeneracy a number of polynucleotide sequences will encode the same polypeptide. Thus, for instance, variants of NH1 are specifically covered by the terms "NH1 nucleic acid", "NH1 polynucleotide" and their equivalents. In addition, such terms specifically include those full length sequences substantially identical (determined as described below) with, for instance, a NH1 polynucleotide sequence and that encode proteins that retain the function of the NH1 polypeptide (e.g., resulting from conservative substitutions of amino acids in the NH1 polypeptide).

A "defense-related" gene refers to a plant nucleic acid whose expression increases when a plant is contacted with, or infected by, a pathogen. One of ordinary skill in the art will recognize that defense-related genes encode polypeptides with diverse predicted functions. Typically, defense-related genes encode polypeptides that may inhibit or destroy an invading pathogen or pathogen product. For instance, several defense-related genes are predicted to encode chitinases that can destroy the cell wall of invading fungal pathogens. The expression of many defense related genes is also induced or increased upon exposure to salicylic acid (SA) or SA analogs such as 2,6-dichloroisonicotinic acid (INA). Examples of defense-related genes include genes that encode pathogenesis-related proteins (PR) (see, e.g., Ward, et al. *Plant Cell* 3:1085–1094 (1991); Reuber et al. *Plant J.* 16(4):473–85 (1998); Heitz T, et al. *Mol Gen Genet* 245(2):246–54 (1994); and Stintzi et al. *Biochimie* 75(8):687–706 (1993)). Pathogenesis proteins include several proteins with homology to proteins with functions including β-1,3-glucanase and chitinases. Not all PR proteins have predicted functions (e.g., PR-1). Other examples of defense related genes include those encoding phytoalexins, phenylalanine ammonia lyase (PAL), proteinases, peroxidases, glutathoine-S transferases, lipoxygenases, as well as genes such as the rice Pir7b gene (see, e.g., Waspi, et al., *Eur. J. Biochem.* 254(1):32–7 (1998)), and SRG1 and SRG2 from alfalfa (see, e.g., Truesdell & Dickman, *Plant Mol. Biol.* 33(4):737–43 (1997)), which were identified by the characteristic of induction upon pathogen infection. See, e.g., Hunt, et al. *Gene* 179(1):89–95 (1996); Fluhr, et al. *Biochem Soc Symp* 60:131–41 (1994); Bowles, et al. *Annu Rev Biochem* 59:873–907 (1990); Glazebrook, et al. *Annu Rev Genet* 31:547–69 (1997); Dixon, R., et al., *Adv Genet.* 28:165–234 (1990); Ward, E., et al., *Plant Cell* 3:1085–1094 (1991); Lawton, et al., *Plant J.* 10:71–82 (1996); and Friedrich, L., et al., *Plant J.* 10:61–70 (1996) for additional examples and reviews of defense-related genes.

"Pathogens" include, but are not limited to, viruses, bacteria, nematodes, fungi or insects (see, e.g., Agrios, *Plant Pathology* (Academic Press, San Diego, Calif.) 1988).

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, CABIOS 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising ANT nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

DESCRIPTION OF THE SPECIFIC EMBODIMENTS

The present invention provides the first identification and characterization of the rice polypeptide sequence, PNI. The present invention also provides the first identification and characterization of the rice polypeptide sequences that interact with the polypeptides PNI and MN1. The present invention also provides the polynucleotide sequences encoding such polypeptides as well as methods of enhancing resistance to pathogens by introducing the polynucleotides into plants. PNI and MN1 were originally identified by their characteristics of interacting with the *Arabidopsis* NPR1 polypeptide in a yeast two hybrid system. The present invention provides for polynucleotides that encode three polypeptides that interact with MN1. One polypeptide, MAP1A, has homology to rat microtubule associated protein 1A. The two other polypeptides, GRL1 and GRL2, have homology to glutaredoxin proteins.

The present invention also provides for polynucleotides that encode five polypeptides that interact with PNI. Two of the polypeptides, NH1 and NH2 have homology to the Arabidopsis NPR1 protein. Of the remaining three polypeptides, one has homology to Arabidopsis nucleolins, one has homology to the Arabidopsis PREG-like protein, and the third does not display homology with any known polypeptide sequence.

Increasing Polypeptide Activity or Gene Expression

Any of a number of means well known in the art can be used to increase activity of polypeptides or polynucleotides of the invention in plants. Enhanced expression is useful, for example, to enhance systemic resistance to pathogens. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, one or several genes of the invention can be expressed constitutively (e.g., using the CaMV 35S promoter).

Increased activity or expression of polypeptides of polynucleotides of the invention can also be used to enhance resistance of plants to specific pathogens. For instance, expression of gene products that interact with PNI or MN1 can be targeted to induce defense-related genes harmful to specific pathogens.

Increasing Gene Expression

Isolated sequences prepared as described herein can be used to introduce expression of a particular nucleic acid to increase gene expression using methods well known to those of skill in the art. Preparation of suitable constructs and means for introducing them into plants are described below.

One of skill will recognize that the polypeptides encoded by the genes of the invention, like other proteins, have different domains that perform different functions. Thus, gene sequences of the invention need not be full length, so long as the desired functional domain of the protein is expressed.

Modified protein chains can also be readily designed utilizing various recombinant DNA techniques well known to those skilled in the art and described in detail below. For example, the chains can vary from the naturally occurring sequence at the primary structure level by amino acid substitutions, additions, deletions, and the like. These modifications can be used in a number of combinations to produce the final modified protein chain.

Modification of Endogenous Genes of the Invention

Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays, fast neutrons or gamma rays can be used.

Alternatively, homologous recombination can be used to induce targeted gene modifications by specifically targeting gene of the invention in vivo (see, generally, Grewal and Klar, *Genetics* 146: 1221–1238 (1997) and Xu et al., *Genes Dev.* 10: 2411– 2422 (1996)). Homologous recombination has been demonstrated in plants (Puchta et al., *Experientia* 50: 277–284 (1994), Swoboda et al., *EMBO J.* 13: 484–489 (1994); Offringa et al., *Proc. Natl. Acad. Sci. USA* 90: 7346–7350 (1993); and Kempin et al. *Nature* 389:802–803 (1997)).

In applying homologous recombination technology to the genes of the invention, mutations in selected portions of a gene sequence of the invention (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91: 4303–4307 (1994); and Vaulont et al., *Transgenic Res.* 4: 247–255 (1995) are conveniently used to increase the efficiency of selecting for altered gene expression in transgenic plants. The mutated gene will interact with the target wild-type gene in such a way that homologous recombination and targeted replacement of the wild-type gene will occur in transgenic plant cells, resulting in suppression of activity associated with a wild type gene of the invention.

Alternatively, oligonucleotides composed of a contiguous stretch of RNA and DNA residues in a duplex conformation with double hairpin caps on the ends can be used. The RNA/DNA sequence is designed to align with the sequence of the target gene and to contain the desired nucleotide change. Introduction of the chimeric oligonucleotide on an extrachromosomal T-DNA plasmid results in efficient and specific gene conversion directed by chimeric molecules in a small number of transformed plant cells. This method is described in Cole-Strauss et al., *Science* 273:1386–1389 (1996) and Yoon et al. *Proc. Natl. Acad. Sci. USA* 93: 2071–2076 (1996).

Other Means for Increasing Activity of Polynucleotides and Polypeptides of the Invention One method to increase expression of genes of the invention is to use "activation mutagenesis" (see, e.g. Hiyashi et al. *Science* 258:1350–1353 (1992)). In this method an endogenous gene of the invention can be modified to be expressed constitutively, ectopically, or excessively by insertion of T-DNA sequences that contain strong/constitutive promoters upstream of the endogenous gene. As explained below, preparation of transgenic plants overexpressing a gene of the invention can also be used to increase expression of that gene. Activation mutagenesis of the endogenous gene of the invention will give the same effect as overexpression of a transgenic nucleic acid of the invention in transgenic plants. Alternatively, an endogenous gene encoding an enhancer of activity or expression of an endogenous gene of the invention can be modified to be expressed by insertion of T-DNA sequences in a similar manner and activity of genes or polypeptides of the invention can be increased.

Another strategy to increase gene expression can be the use of dominant hyperactive mutants of a gene of the invention by expressing modified transgenes. For example, expression of modified NH1 with a defective domain that is important for interaction with a negative regulator of NH1 activity can be used to generate dominant hyperactive NH 1 proteins. Alternatively, expression of truncated NH 1 proteins which have only a domain that interacts with a negative regulator can titrate the negative regulator and thereby increase endogenous NH1 activity. Use of dominant mutants to hyperactivate target genes is described in Mizukami et al. *Plant Cell* 8:831–845 (1996).

Inhibition of Activity or Expression of Polynucleotides or Polypeptides of the Invention Activity of polynucleotides or polypeptides of the invention is important in modulating, directly or indirectly, the expression of a number of defense-related genes through interaction with the genes' promoters as well as with other proteins (e.g., RNA polymerase, transcription factors and the like). For those polynucleotides or polypeptides of the invention that act to down regulate defense-related genes, inhibition of such gene expression activity can be used, for instance, to increase pathogen resistance in plants. Alternatively, inhibition of polynucleotides or polypeptides of the invention that activate defense related genes can reduce pathogen resistance in plants. In particular, targeted expression of nucleic acids of the invention that inhibit endogenous gene expression (e.g., antisense or co-suppression) can be used to reduce pathogen resistance.

Inhibition of Gene Expression

The nucleic acid sequences disclosed here can be used to design nucleic acids useful in a number of methods to inhibit expression of genes of the invention in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque, *Plant Sci.* (Limerick) 105: 125–149 (1995); Pantopoulos, In Progress in Nucleic Acid Research and Molecular Biology, Vol. 48. Cohn, W. E. and K. Moldave (Ed.). Academic Press, Inc.: San Diego, Calif., USA; London, England, UK. p. 181–238; Heiser et al., *Plant Sci.* (*Shannon*) 127: 61–69 (1997)) and by preventing the accumulation of mRNA which encodes the protein of interest, (see, Baulcombe, *Plant Mol. Bio.* 32:79–88 (1996); Prins and Goldbach, *Arch. Virol.* 141: 2259–2276 (1996); Metzlaff et al. *Cell* 88: 845–854 (1997), Sheehy et al., *Proc. Nat. Acad. Sci. USA*, 85:8805–8809 (1988), and Hiatt et al., U.S. Pat. No. 4,801,340).

The nucleic acid segment to be introduced generally will be substantially identical to at least a portion of the endogenous gene or genes (e.g., NH1, PNI, etc.) to be repressed. The sequence, however, need not be perfectly identical to inhibit expression. The vectors of the present invention can be designed such that the inhibitory effect applies to other genes within a family of genes exhibiting identity or substantial identity to the target gene.

For antisense suppression, the introduced sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides to about the full length of a nucleotide should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress expression of genes of the invention. The targets can include, for instance, the coding regions, introns, sequences from exon/intron junctions, 5' or 3' untranslated regions, and the like.

Another well-known method of suppression is sense co-suppression. Introduction of nucleic acid configured in the sense orientation has been recently shown to be an effective means by which to block the transcription of target genes. For an example of the use of this method to modulate expression of endogenous genes (see, Assaad et al., *Plant Mol. Bio.* 22: 1067–1085 (1993); Flavell, *Proc. Natl. Acad. Sci. USA* 91: 3490–3496 (1994); Stam et al., *Annals Bot.* 79: 3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity is most preferred. As with antisense regulation, the effect should apply to any other proteins within a similar family of genes exhibiting identity or substantial identity.

For co-suppression, the introduced sequence, needing less than absolute identity, also need not be full length, relative to either the primary transcription product or fully processed mRNA. This may be preferred to avoid concurrent production of some plants that over-express the introduced sequence. A higher identity in a sequence shorter than full-length compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using co-suppression technologies.

Oligonucleotide-based triple-helix formation can also be used to disrupt expression of genes of the invention. Triplex DNA can inhibit DNA transcription and replication, generate site-specific mutations, cleave DNA, and induce homologous recombination (see, e.g., Havre and Glazer *J. Virology* 67:7324–7331 (1993); Scanlon et al. *FASEB J.* 9:1288–1296 (1995); Giovannangeli et al. *Biochemistry* 35:10539–10548 (1996); Chan and Glazer *J. Mol. Medicine* (*Berlin*) 75: 267–282 (1997)). Triple helix DNAs can be used to target the same sequences identified for antisense regulation.

Catalytic RNA molecules or ribozymes can also be used to inhibit expression of genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick, *Nature* 365:448–451 (1993); Eastham and Ahlering, *J. Urology* 156:1186–1188 (1996); Sokol and Murray, *Transgenic Res.* 5:363–371 (1996); Sun et al., *Mol. Biotechnology* 7:241–251 (1997); and Haseloff et al., *Nature,* 334:585–591 (1988).

Modification of Endozenous Genes of the Invention

Methods for introducing genetic mutations described above can also be used to select for plants with decreased expression of genes of the invention.

Other Means for Inhibiting Polynucleotide or Polypeptide Activity

Activity of polynucleotides of the invention may be modulated by eliminating the proteins that are required for cell-specific expression of such polynucleotides. Thus, expression of regulatory proteins and/or the sequences that control gene (e.g., NH1, NH2, PNI, etc.) expression can be modulated using the methods described here.

Another strategy is to inhibit the ability of a protein of the invention to interact with itself or with other proteins. This can be achieved, for instance, using antibodies specific to a polypeptide of the invention. In this method expression of antibodies specific for a polypeptide of the invention is used to inactivate functional domains through antibody:antigen recognition (see, Hupp et al., *Cell* 83:237–245 (1995)). Interference with activity of protein(s) that interact with polypeptides of the invention can be applied in a similar fashion. Alternatively, dominant negative alleles (i.e. dominant gain of function mutants) of the genes of the invention can be prepared by expressing a transgene that encodes a truncated polypeptide. For example, a dominant negative allele of NH1 can be created by expressing a truncated NH1 polypeptide. Use of dominant negative mutants to inactivate target genes in transgenic plants is described in Mizukami et al., *Plant Cell* 8:831–845 (1996).

Purification of Polypeptides

Naturally occurring or recombinant polypeptides of the invention can be purified for use in functional assays. Naturally occurring polypeptides can be purified, e.g., from plant tissue and any other source of the desired polypeptide. Recombinant polypeptides can be purified from any suitable expression system.

The polypeptides of the invention may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant polypeptides are being purified. For example, proteins having established molecular adhesion properties can be reversibly fused to polypeptides of the invention. With the appropriate ligand, the such polypeptides can be selectively adsorbed to a purification column and then freed from the column in a relatively pure form. The fused protein is then removed by enzymatic activity. Finally the polypeptides of the invention could be purified using immunoaffinity columns.

Isolation of Nucleic Acids of the Invention

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998).

The isolation of nucleic acids of the invention may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaves, and a cDNA library that contains a gene transcript of the invention is prepared from the mRNA. Alternatively, cDNA may be prepared from mRNA extracted from other tissues in which genes of the invention or homologs are expressed.

The cDNA or genomic library can then be screened using a probe based upon the sequence of a cloned gene of the invention as disclosed here. Probes may be used to hybridize with genomic DNA or cDNA sequences to isolate homologous genes in the same or different plant species. Alternatively, antibodies raised against a polypeptide of the invention can be used to screen an mRNA expression library.

Alternatively, the nucleic acids of interest can be amplified from nucleic acid samples using amplification techniques. For instance, polymerase chain reaction (PCR) technology can be used to amplify the sequences of genes of the invention directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR, see *PCR Protocols: A Guide to Methods and Applications*. (Innis, M, Gelfand, D., Sninsky, J. and White, T., eds.), Academic Press, San Diego (1990). Appropriate primers and probes for identifying sequences of the invention from plant tissues are generated from comparisons of the sequences provided here (e.g. SEQ ID NO: 1, SEQ ID NO:3, etc.).

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant.

Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Constitutive promoters and regulatory elements can also be isolated from genes that are expressed constitutively or at least expressed in most if not all tissues of a plant. Such genes include, for example, ACT11 from *Arabidopsis* (Huang et al. *Plant Mol. Biol.* 33:125–139 (1996)), Cat3 from *Arabidopsis* (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol.* 208:551–565 (1989)), and Gpc2 from maize (GenBank No. U45855, Manjunath et al., *Plant Mol. Biol.* 33:97–112 (1997)).

Alternatively, the plant promoter may direct expression of a nucleic acid of the invention in a specific tissue, organ or cell type (i.e. tissue-specific promoters) or may be otherwise under more precise environmental or developmental control (i.e. inducible promoters). Examples of environmental conditions that may effect transcription by inducible promoters include anaerobic conditions, elevated temperature, the presence of light, or sprayed with chemicals/hormones. Tissue-specific promoters can be inducible. Similarly, tissue-specific promoters may only promote transcription within a certain time frame of developmental stage within that tissue. Other tissue specific promoters may be active throughout the life cycle of a particular tissue. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissue-specific promoters can also be used in the invention. For instance, promoters that direct expression of nucleic acids in leaves, roots or flowers are useful for enhancing resistance to pathogens that infect those organs. For expression of a polynucleotide of the invention in the aerial vegetative organs of a plant, photosynthetic organ-specific promoters, such as the RBCS promoter (Khoudi, et al., *Gene* 197:343, 1997), can be used. Root-specific expression of polynucleotides of the invention can be achieved under the control of the root-specific ANR1 promoter (Zhang & Forde, *Science*, 279:407, 1998). Any strong, constitutive promoters, such as the CaMV 35S promoter, can be used for the expression of polynucleotides of the invention throughout the plant.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *EMBO. J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon,*

*Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna,* and *Zea.*

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of mRNA or protein of the invention in transgenic plants. Means for detecting and quantitating mRNAs or proteins are well known in the art.

Methods of Enhancing Plant Resistance to Pathogens

The present invention provides for method of enhancing plant resistance to pathogens by modulating the expression and/or activity of polynucleotides and/or polypeptides of the invention. Without limiting the invention to a particular mechanism of operation, polypeptides of the invention are likely to act as direct or indirect modulators of defense-related genes. Thus, resistance can be enhanced, for instance, by increased expression of positive regulators of defense-related genes. Alternatively, or in combination, polynucleotides or polypeptides of the invention can be modified to enhance resistance, e.g., by increasing or decreasing the polypeptides' interactions with other components important in plant pathogen resistance.

Without limiting the invention to a particular mechanism of operation, one possible mechanism by which the polypeptides of the invention modulate resistance is, for example, by acting as components of a signal cascade between initiation of resistance and the development of the resistance response. For example, interaction of polypeptides of the invention with defense-related promoters may lead directly to increased transcription of defense-related transcripts, thereby enhancing resistance to pathogens.

Alternatively, polypeptides of the invention may interact with promoters of other genes as well as with other regulatory factors, thereby modulating expression of defense related genes or other genes involved in resistance. For example, after a plant component (e.g., a plant disease resistance polypeptide) is activated by the presence of a pathogen (e.g. through an avirulence determinant, see, e.g., Dangl, *Curr Top Microbiol Immunol* 192:99–118 (1994)), the plant component provides a signal (e.g., via protein—protein interactions, phosphorylation/dephosphorylation, oxidative burst or the like) directly or indirectly, to the polypeptides of the invention (e.g. NH1, NH2, PNI, etc.). NH1, for example, may then activate MN1 and/or PNI polypeptides that in turn activate defense-related genes as well as polynucleotides and polypeptides of the invention (e.g., SEQ ID NO:8, SEQ ID NO:10, SEQ ID NO:12, SEQ ID NO:14, SEQ ID NO:16, and SEQ ID NO:18).

Alternatively, some polypeptides of the invention may act as negative regulator of a resistance response. Negative regulators act to prevent a resistance response by various mechanisms (e.g., via protein—protein interactions, phosphorylation/dephosphorylation, etc.). For instance, polypeptides of the invention may act as transcriptional repressors, thereby allowing for the expression of defense-related genes. Such mechanisms may be altered when a plant is contacted with a pathogen, allowing a resistance response to develop.

Selecting for Plants with Enhanced Resistance

Plants with enhanced resistance can be selected in many ways. One of ordinary skill in the art will recognize that the following methods are but a few of the possibilities. One method of selecting plants with enhanced resistance is to determine resistance of a plant to a specific plant pathogen. Possible pathogens include, but are not limited to, viruses, bacteria, nematodes, fungi or insects (see, e.g., Agrios, *Plant Pathology* (Academic Press, San Diego, Calif.) (1988)). One of skill in the art will recognize that resistance responses of plants vary depending on many factors, including what pathogen or plant is used. Generally, enhanced resistance is measured by the reduction or elimination of disease symptoms when compared to a control plant. In some cases, however, enhanced resistance can also be measured by the production of the hypersensitive response (HR) of the plant (see, e.g., Staskawicz et al. *Science* 268(5211): 661–7 (1995)). Plants with enhanced resistance can produce an enhanced hypersensitive response relative to control plants.

Enhanced resistance can also be determined by measuring the increased expression of a gene operably linked a defense related promoter. Measurement of such expression can be measured by quantitating the accumulation of RNA or subsequent protein product (e.g., using northern or western blot techniques, respectively (see, e.g., Sambrook et al. and Ausubel et al.). A possible alternate strategy for measuring defense gene promoter expression involves operably linking a reporter gene to the promoter. Reporter gene constructs allow for ease of measurement of expression from the promoter of interest. Examples of reporter genes include: β-gal, GUS (see, e.g., Jefferson, R. A., et al., *EMBO J* 6: 3901–3907 (1987), green fluorescent protein, luciferase, and others.

The following Examples are offered by way of illustration, not limitation.

EXAMPLE 1

This example shows that four rice bZIP gene products, MN1, MN8, MN38 and MN140, and a proline-rich protein, PNI, bind to *Arabidopsis* NPR1 in the yeast two-hybrid system.

Results

Five Rice Polypeptides Interact with NPR1 in the Yeast Two-Hybrid System.

A rice cDNA library prepared in the pAD-GAL4 vector was screened using a full-length *Arabidopsis* Npr1 cDNA as the bait. The *Arabidopsis* Npr1 bait was cloned into the SmaI and BglII sites of plasmid pMC86, which was constructed by replacing the GAL4 activation domain in pPC86 (Chevray, P. M. and Nathans, D., *Proc. Natl. Acad. Sci. USA* 89:5789–5793 (1992)) with the GAL4 DNA binding domain (GAL4DB) in pPC97 by using KpnI and SacI sites. NPR1 was expressed as a GAL4 DB::NPR1 fusion protein in the yeast host HF7c (Clontech, Palo Alto, Calif.). The yeast two-hybrid screen was performed as described (Finley, R. L. et al. (1996) in *DNA Cloning—Expression Systems: A Practical Approach*, eds. Glover D. & Hames B. D (Oxford University Press, Oxford, England), pp. 169–203). After screening approximately 20 million yeast transformants, five independent clones were isolated that displayed histidine prototrophy and were lacZ positive. Each isolated clone was then used to transform HF7c together with the pMC86 plasmid or with pMC86 containing the bait, confirming specificity of the interaction. These clones are hereafter called PNI, MN 1, MN8, MN38, and MN140.

The 5' ends of MN1 and MN8 cDNAs were obtained by running nested PCR reactions for each clones using the same rice library cDNA as the template. The primary reaction was carried out with anchor primer SS20 (5'AGGGATGTT-TAATACCACTAC; SEQ ID No:21) and gene-specific primer mn1-1 (5'GAAGCCATGACTGCACCA; SEQ ID No:22) for MN1 primer mn8-1 (5'TTATCGTCGGTATC-CAGGA; SEQ ID No:23) for MN8. The secondary reaction used anchor primer ADR1 (5'ACCCGGGAGAGATC-GAATTCGGCACGA; SEQ ID No:24) and gene-specific primer mn1-2 (5'CACCACTATGTCCGTTTTC; SEQ ID No:25) for MN1 or primer mn8-2 (5'GGACTGTTGATGT-GTCAGT; SEQ ID No:26) for MN8. PCR products were cloned in the pCR-BluntII-TOPO (Invitrogen, Carlsbad, Calif.) plasmid vector. Two clones for each were sequenced. The MN8 clone obtained from two-hybrid screens appeared to contain the complete cDNA coding region when the sequences were compared. The MN1 sequence encoding the first 18 amino acids was combined with that of the original MN1 clone to give a complete cDNA coding sequence.

EXAMPLE 2

This example shows the identification of three polypeptides that interact with MN1 in the yeast two-hybrid system.

Results

Three Polypeptides that Interact with MN1 were Identified.

The rice cDNA library described above was rescreened using a truncated MN1, containing amino acids 98 to 334, as bait in the yeast two-hybrid system. The MN1 bait was cloned into the SmaI and SpeI sites of plasmid pMC86. MN1 was expressed as a GAL4 DB::MN1 fusion protein in the yeast host HF7c. After screening approximately five million yeast transformants, twenty independent clones were isolated that displayed histidine prototrophy and were lacZ positive. After nucleotide sequence analysis, three unique predicted protein sequences were identified (SEQ ID No:14, SEQ ID NO:16 and SEQ ID NO:18, encoded by SEQ ID NO:13, SEQ ID NO:15 and SEQ ID NO:17, respectively).

These clones are designated GRL1, GRL2 and MAP1A, respectively.

As suggested by their names, GRL1 and GRL2 demonstrate homology to glutaredoxin. MAP1A has partial homology with the rat microtubule associated protein 1A.

EXAMPLE 3

This example shows the identification of five polypeptides that interact with PNI in the yeast two-hybrid system.

Results

Five Polypeptides that Interact with PNI were Identified.

The rice cDNA library described above was again rescreened, this time using full length PNI as bait in the yeast two-hybrid system. The PNI bait was cloned into the SmaI and SpeI sites of plasmid pMC86. PNIs expressed as a GAL4 DB::PNI fusion protein in the yeast host HF7c (Clontech, Palo Alto, Calif.). After screening approximately sixteen million yeast transformants, five independent clones were isolated that displayed histidine prototrophy and were lacZ positive.

After nucleotide sequence analysis, these five unique predicted protein sequences were identified (see SEQ ID NO:4, SEQ ID NO:6 and SEQ ID NO:8, SEQ ID NO:10, and SEQ ID NO:12 encoded by SEQ ID NO:3, SEQ ID NO:5 and SEQ ID NO:7, SEQ ID NO:9, and SEQ ID NO:11, respectively). The first two clones have homology to Arabidopsis NPR1 and therefore are called NH1 (NPR1 homolog 1), NH2 (NPR1 homolog 2). The third protein (SEQ ID NO:8) has homology to an Arabidopsis nucleolin-like protein. The fourth protein (SEQ ID NO:10) has homology to an Arabidopsis PREG-like protein. Finally, SEQ ID NO:12 does not have significant homology to anything in the current databases.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

---

What is claimed is:

1. An isolated polynucleotide encoding a polypeptide that is at least 95% identical to SEQ ID NO:4, wherein the polynucleotide, when introduced into a plant, enhances the plant's resistance to pathogens compared to resistance of a plant not transformed with the polynucleotide, and
wherein a first amino acid sequence comprising the polypeptide binds to a second amino acid sequence comprising SEQ ID NO:2 in a yeast two-hybrid binding assay.

2. The polynucleotide of claim 1, wherein the polynucleotide is from a rice plant.

3. The polynucleotide of claim 1, wherein the polynucleotide is SEQ ID NO:3.

4. The polynucleotide of claim 1, wherein the polynucleotide encodes SEQ ID NO:4.

5. A construct comprising the polynucleotide of claim 1, operably linked to a promoter.

6. The construct of claim 5, wherein the promoter is constitutive.

7. The construct of claim 5, wherein the promoter is inducible.

8. The construct of claim 5, wherein the promoter is tissue-specific.

9. A transgenic plant comprising a recombinant expression cassette comprising a plant promoter operably linked to a polynucleotide encoding a polypeptide that is at least 95% identical to SEQ ID NO:4, wherein the polynucleotide, when introduced into a plant, enhances the plant's resistance to pathogens compared to resistance of a plant not transformed with the polynucleotide, and
wherein a first amino acid sequence comprising the polypeptide binds to a second amino acid sequence comprising SEQ ID NO:2 in a yeast two-hybrid binding assay.

10. The transgenic plant of claim 9, wherein the plant is rice.

11. The transgenic plant of claim 9, wherein the polynucleotide is SEQ ID NO:3.

12. The transgenic plant of claim 9, wherein the polynucleotide encodes SEQ ID NO:4.

13. The transgenic plant of claim 9, wherein the plant promoter is constitutive.

14. The transgenic plant of claim 9, wherein the plant promoter is inducible.

15. The transgenic plant of claim 9, wherein the plant promoter is tissue-specific.

16. A method of enhancing resistance to pathogens in a plant, the method comprising
1) introducing into the plant a recombinant expression cassette comprising a plant promoter operably linked to a polynucleotide, wherein the polynucleotide encodes a polypeptide that is at least 95% identical to SEQ ID NO:4, wherein a first amino acid sequence comprising the polypeptide binds with a second amino acid sequence comprising SEQ ID NO:2 when assayed in a yeast two-hybrid binding assay; and 2) selecting a plant with enhanced pathogen resistance compared to resistance of a plant not transformed with the recombinant expression cassette.

17. The method of claim 16, wherein the polypeptide comprises SEQ ID NO:4.

18. The method of claim 16, wherein the plant promoter is constitutive.

19. The method of claim 16, wherein the plant promoter is inducible.

20. The method of claim 16, wherein the plant promoter is tissue-specific.

21. The method of claim 16, wherein the plant is from the genus *Oryza*.

* * * * *

SEQUENCE LISTING

<160> NUMBER OF SEQ ID NOS: 26

<210> SEQ ID NO 1
<211> LENGTH: 700
<212> TYPE: DNA
<213> ORGANISM: Oryza sativa
<220> FEATURE:
<221> NAME/KEY: CDS
<222> LOCATION: (1)..(393)
<223> OTHER INFORMATION: proline-rich NPR1 interactor (PNI)

<400> SEQUENCE: 1

```
atg gac gcc acc acc acg gac gcc acc acc gcc aag cgc aag cgc cca      48
Met Asp Ala Thr Thr Thr Asp Ala Thr Thr Ala Lys Arg Lys Arg Pro
 1               5                  10                  15 gcc gcc tcc gac atc gcc gac gac gcc ccc acc acc gtc gac gag gtc      96
Ala Ala Ser Asp Ile Ala Asp Asp Ala Pro Thr Thr Val Asp Glu Val
             20                  25                  30
```

```
tcc gac gcc gag gtc gag gag ttc tac gcc atc ctc cgc cgc atg cgc      144
Ser Asp Ala Glu Val Glu Glu Phe Tyr Ala Ile Leu Arg Arg Met Arg
         35                  40                  45 gac gcc acc cga cgg ctc ggc gcc cgc cct ccc ccg cgc gcg ccg          192
Asp Ala Thr Arg Arg Leu Gly Ala Arg Pro Pro Pro Arg Ala Pro
     50                  55                  60 gcg tgg cgc ccc agc ttc tcc tgg gag gac ttc gcc gac gcg ccg          240
Ala Trp Arg Pro Ser Phe Ser Trp Glu Asp Phe Ala Asp Ala Pro
 65                  70                  75                  80 aag cag gcg ccg ccg ccg cag cag ccc gcc gac cac gag cgc gtc          288
Lys Gln Ala Pro Pro Pro Gln Gln Pro Ala Asp His Glu Arg Val
                 85                  90                  95 gcc gag aac gcc acc ccg ccc cgg cgc ccg gcg ccc ggc ctc gac ctg      336
Ala Glu Asn Ala Thr Pro Pro Arg Arg Pro Ala Pro Gly Leu Asp Leu
             100                 105                 110 aac gtc gag ccg ccg tcc gac gcg ccg gcc acg ccg cgc tcg gcg cgc      384
Asn Val Glu Pro Pro Ser Asp Ala Pro Ala Thr Pro Arg Ser Ala Arg
             115                 120                 125 gcc ccg gca taggcgcgcg ccacgaggaa acgcggcgcg tcgcgcatgc              433
Ala Pro Ala
    130 gggtgctcac ggattacaac tactttgcta gctagaagca gctagctgca gtgttggatt    493 gatccatcca tggagctgcc ttgtcctcct tgtgtgtgaa caggtgagac ctggttaatc    553 aatcgctctt gctgggaaga acaatccat tattggtccc atcatggaga tgtactatca     613 tgtaccaaga caaatgacg ggtttaatta attacccct atattattcg ttctgtaatt      673 cagtaaaaaa aaaaaaaaaa aaaaaaa                                        700

<210> SEQ ID NO 2
<211> LENGTH: 131
<212> TYPE: PRT
<213> ORGANISM: Oryza sativa

<400> SEQUENCE: 2

Met Asp Ala Thr Thr Asp Ala Thr Thr Ala Lys Arg Lys Arg Pro
  1               5                  10                  15

Ala Ala Ser Asp Ile Ala Asp Asp Ala Pro Thr Thr Val Asp Glu Val
                 20                  25                  30

Ser Asp Ala Glu Val Glu Glu Phe Tyr Ala Ile Leu Arg Arg Met Arg
         35                  40                  45

Asp Ala Thr Arg Arg Leu Gly Ala Arg Pro Pro Pro Arg Ala Pro
     50                  55                  60

Ala Trp Arg Pro Ser Phe Ser Trp Glu Asp Phe Ala Asp Ala Pro Pro
 65                  70                  75                  80

Lys Gln Ala Pro Pro Pro Gln Gln Pro Ala Asp His Glu Arg Val
                 85                  90                  95

Ala Glu Asn Ala Thr Pro Pro Arg Arg Pro Ala Pro Gly Leu Asp Leu
             100                 105                 110

Asn Val Glu Pro Pro Ser Asp Ala Pro Ala Thr Pro Arg Ser Ala Arg
             115                 120                 125

Ala Pro Ala
    130

<210> SEQ ID NO 3
<211> LENGTH: 2040
```

```
<212> TYPE: DNA
<213> ORGANISM: Oryza sativa
<220> FEATURE:
<221> NAME/KEY: CDS
<222> LOCATION: (1)..(1746)
<223> OTHER INFORMATION: NPR1 homologue 1 (NH1) protein that interacts
      with PNI protein

<400> SEQUENCE: 3
```

| | | | | | | | | | | | | | | | | |
|---|---|---|---|---|---|---|---|---|---|---|---|---|---|---|---|---|
| atg | gag | ccg | ccg | acc | agc | cac | gtc | acc | aac | gcg | ttc | tcc | gac | tcg | gac | 48 |
| Met | Glu | Pro | Pro | Thr | Ser | His | Val | Thr | Asn | Ala | Phe | Ser | Asp | Ser | Asp | |
| 1 | | | | 5 | | | | | 10 | | | | | 15 | | |
| agc | gcg | tcc | gtg | gag | gag | ggg | gac | gcc | gac | gcg | gac | gcc | gac | gtg | gag | 96 |
| Ser | Ala | Ser | Val | Glu | Glu | Gly | Asp | Ala | Asp | Ala | Asp | Ala | Asp | Val | Glu | |
| | | | 20 | | | | | 25 | | | | | 30 | | | |
| gcg | ctc | cgc | cgc | ctc | tcc | gac | aac | ctc | gcc | gcg | gcg | ttc | cgc | tcg | ccc | 144 |
| Ala | Leu | Arg | Arg | Leu | Ser | Asp | Asn | Leu | Ala | Ala | Ala | Phe | Arg | Ser | Pro | |
| | | 35 | | | | | 40 | | | | | 45 | | | | |
| gag | gac | ttc | gcg | ttc | ctc | gcc | gac | gcg | cgc | atc | gcc | gtc | ccg | ggc | ggc | 192 |
| Glu | Asp | Phe | Ala | Phe | Leu | Ala | Asp | Ala | Arg | Ile | Ala | Val | Pro | Gly | Gly | |
| | 50 | | | | | 55 | | | | | 60 | | | | | |
| ggc | ggc | ggc | ggc | ggc | gac | ctg | cgg | gtg | cac | cgc | tgc | gtg | ctc | tcc | gcg | 240 |
| Gly | Gly | Gly | Gly | Gly | Asp | Leu | Arg | Val | His | Arg | Cys | Val | Leu | Ser | Ala | |
| 65 | | | | | 70 | | | | | 75 | | | | | 80 | |
| cgg | agc | ccc | ttc | ctg | cgc | ggc | gtc | ttc | gcg | cgc | cgc | gcc | gcc | gcc | gcc | 288 |
| Arg | Ser | Pro | Phe | Leu | Arg | Gly | Val | Phe | Ala | Arg | Arg | Ala | Ala | Ala | Ala | |
| | | | | 85 | | | | | 90 | | | | | 95 | | |
| gca | ggc | ggc | ggc | ggc | gag | gat | ggc | agc | gag | agg | ctg | gag | ctc | cgg | gag | 336 |
| Ala | Gly | Gly | Gly | Gly | Glu | Asp | Gly | Ser | Glu | Arg | Leu | Glu | Leu | Arg | Glu | |
| | | | | 100 | | | | | 105 | | | | | 110 | | |
| ctc | ctc | ggc | ggc | ggc | ggc | gag | gag | gtg | gag | gtc | ggg | tac | gag | gcg | ctg | 384 |
| Leu | Leu | Gly | Gly | Gly | Gly | Glu | Glu | Val | Glu | Val | Gly | Tyr | Glu | Ala | Leu | |
| | | | 115 | | | | | 120 | | | | | 125 | | | |
| cgg | ctg | gtg | ctc | gac | tac | ctc | tac | agc | ggc | cgc | gtc | ggc | gac | ctg | ccc | 432 |
| Arg | Leu | Val | Leu | Asp | Tyr | Leu | Tyr | Ser | Gly | Arg | Val | Gly | Asp | Leu | Pro | |
| | 130 | | | | | 135 | | | | | 140 | | | | | |
| aag | gcg | gcg | tgc | ctc | tgc | gtc | gac | gag | gac | tgc | gcc | cac | gtc | ggg | tgc | 480 |
| Lys | Ala | Ala | Cys | Leu | Cys | Val | Asp | Glu | Asp | Cys | Ala | His | Val | Gly | Cys | |
| 145 | | | | | 150 | | | | | 155 | | | | | 160 | |
| cac | ccc | gcc | gtc | gcg | ttc | atg | gcg | cag | gtc | ctc | ttc | gcc | gcc | tcc | acc | 528 |
| His | Pro | Ala | Val | Ala | Phe | Met | Ala | Gln | Val | Leu | Phe | Ala | Ala | Ser | Thr | |
| | | | | 165 | | | | | 170 | | | | | 175 | | |
| ttc | cag | gtc | gcc | gag | ctc | acc | aac | ctc | ttc | cag | cgg | cgt | ctc | ctt | gat | 576 |
| Phe | Gln | Val | Ala | Glu | Leu | Thr | Asn | Leu | Phe | Gln | Arg | Arg | Leu | Leu | Asp | |
| | | | 180 | | | | | 185 | | | | | 190 | | | |
| gtc | ctt | gat | aag | gtt | gaa | gta | gat | aac | ctt | cta | ttg | atc | tta | tct | gtt | 624 |
| Val | Leu | Asp | Lys | Val | Glu | Val | Asp | Asn | Leu | Leu | Leu | Ile | Leu | Ser | Val | |
| | | | 195 | | | | | 200 | | | | | 205 | | | |
| gcc | aac | tta | tgc | aac | aaa | tct | tgc | atg | aaa | ctg | ctt | gaa | aga | tgc | ctt | 672 |
| Ala | Asn | Leu | Cys | Asn | Lys | Ser | Cys | Met | Lys | Leu | Leu | Glu | Arg | Cys | Leu | |
| | 210 | | | | | 215 | | | | | 220 | | | | | |
| gat | atg | gta | gtc | cgg | tca | aac | ctt | gac | atg | att | act | ctt | gag | aag | tca | 720 |
| Asp | Met | Val | Val | Arg | Ser | Asn | Leu | Asp | Met | Ile | Thr | Leu | Glu | Lys | Ser | |
| 225 | | | | | 230 | | | | | 235 | | | | | 240 | |
| ttg | cct | cca | gat | gtt | atc | aag | cag | att | att | gat | gca | cgc | cta | agc | ctc | 768 |
| Leu | Pro | Pro | Asp | Val | Ile | Lys | Gln | Ile | Ile | Asp | Ala | Arg | Leu | Ser | Leu | |
| | | | | 245 | | | | | 250 | | | | | 255 | | |
| gga | tta | att | tca | cca | gaa | aac | aag | gga | ttt | cct | aac | aaa | cat | gtg | agg | 816 |
| Gly | Leu | Ile | Ser | Pro | Glu | Asn | Lys | Gly | Phe | Pro | Asn | Lys | His | Val | Arg | |
| | | | 260 | | | | | 265 | | | | | 270 | | | |
| agg | ata | cac | aga | gcc | ctt | gac | tct | gac | gat | gta | gag | cta | gtc | agg | atg | 864 |

```
                                                        -continued

Arg Ile His Arg Ala Leu Asp Ser Asp Asp Val Glu Leu Val Arg Met
        275                 280                 285 ctg ctc act gaa gga cag aca aat ctt gat gat gcg ttt gca ctg cac      912
Leu Leu Thr Glu Gly Gln Thr Asn Leu Asp Asp Ala Phe Ala Leu His
    290                 295                 300 tac gcc gtc gaa cat tgt gac tcc aaa att aca acc gag ctt ttg gat      960
Tyr Ala Val Glu His Cys Asp Ser Lys Ile Thr Thr Glu Leu Leu Asp
305                 310                 315                 320 ctc gca ctt gca gat gtt aat cat aga aac cca aga ggt tat act gtt     1008
Leu Ala Leu Ala Asp Val Asn His Arg Asn Pro Arg Gly Tyr Thr Val
                325                 330                 335 ctt cac att gct gcg agg cga aga gag cct aaa atc att gtc tcc ctt     1056
Leu His Ile Ala Ala Arg Arg Arg Glu Pro Lys Ile Ile Val Ser Leu
            340                 345                 350 tta acc aag ggg gct cga cca gca gat gtt aca ttc gat ggg aga aaa     1104
Leu Thr Lys Gly Ala Arg Pro Ala Asp Val Thr Phe Asp Gly Arg Lys
        355                 360                 365 gcg gtt caa atc tca aaa aga cta aca aaa caa ggg gat tac ttt ggg     1152
Ala Val Gln Ile Ser Lys Arg Leu Thr Lys Gln Gly Asp Tyr Phe Gly
    370                 375                 380 gtt acc gaa gaa gga aaa cct tct cca aaa gat agg tta tgt att gaa     1200
Val Thr Glu Glu Gly Lys Pro Ser Pro Lys Asp Arg Leu Cys Ile Glu
385                 390                 395                 400 ata ctg gag caa gct gaa aga agg gac cca caa ctc gga gaa gca tca     1248
Ile Leu Glu Gln Ala Glu Arg Arg Asp Pro Gln Leu Gly Glu Ala Ser
                405                 410                 415 gtt tct ctt gca atg gca ggt gag agt cta cga gga agg ttg ctg tat     1296
Val Ser Leu Ala Met Ala Gly Glu Ser Leu Arg Gly Arg Leu Leu Tyr
            420                 425                 430 ctt gaa aac cga gtt gct ttg gca agg att atg ttt ccg atg gag gca     1344
Leu Glu Asn Arg Val Ala Leu Ala Arg Ile Met Phe Pro Met Glu Ala
        435                 440                 445 aga gta gca atg gat att gct caa gtg gat gga act ttg gaa ttt aac     1392
Arg Val Ala Met Asp Ile Ala Gln Val Asp Gly Thr Leu Glu Phe Asn
    450                 455                 460 ctg ggt tct ggt gca aat cca cct cct gaa aga caa cgg aca act gtt     1440
Leu Gly Ser Gly Ala Asn Pro Pro Pro Glu Arg Gln Arg Thr Thr Val
465                 470                 475                 480 gat cta aat gaa agt cct ttc ata atg aaa gaa gaa cac tta gct cgg     1488
Asp Leu Asn Glu Ser Pro Phe Ile Met Lys Glu Glu His Leu Ala Arg
                485                 490                 495 atg aca gca ctc tcc aaa aca gtg gag ctc ggg aaa cgc ttt ttc ccg     1536
Met Thr Ala Leu Ser Lys Thr Val Glu Leu Gly Lys Arg Phe Phe Pro
            500                 505                 510 cga tgt tcg aac gtg ctc gac aag atc atg gat gat gaa act gat ccg     1584
Arg Cys Ser Asn Val Leu Asp Lys Ile Met Asp Asp Glu Thr Asp Pro
        515                 520                 525 gtt tcc ctc gga aga gac acg tcc gcg gag aag agg aag agg ttt cat     1632
Val Ser Leu Gly Arg Asp Thr Ser Ala Glu Lys Arg Lys Arg Phe His
    530                 535                 540 gac ctg cag gat gtt ctt cag aag gca ttc cac gag gac aag gag gag     1680
Asp Leu Gln Asp Val Leu Gln Lys Ala Phe His Glu Asp Lys Glu Glu
545                 550                 555                 560 aat gac agg tcg ggg ctc tcg tcg tcg tcg tca tcg aca tcg atc ggg     1728
Asn Asp Arg Ser Gly Leu Ser Ser Ser Ser Ser Thr Ser Ile Gly
                565                 570                 575 gcc att cga cca agg aga tgaacaccat tgctcccaaa tagttgccat            1776
Ala Ile Arg Pro Arg Arg
        580
```

-continued

```
attgatagct aactgtcctc ctggagctac tcacctgatg gttgccttct gtcaattgcc      1836
ccccaaatat attctcaatg gtttaggctt gtacagtatt agttcttaca gctattgccc      1896
cgtcaattgt gaaacgcaga agtttcacta gtgcttgtac tcgaggtgta atacaagtgc      1956
ttgaattttg agttgtactt ggaatttcca gtggtttgct cgtaaaaatg agatgatttc      2016
ttggcaaaaa aaaaaaaaaa aaaa                                             2040
```

<210> SEQ ID NO 4
<211> LENGTH: 582
<212> TYPE: PRT
<213> ORGANISM: Oryza sativa

<400> SEQUENCE: 4

```
Met Glu Pro Pro Thr Ser His Val Thr Asn Ala Phe Ser Asp Ser Asp
 1               5                  10                  15

Ser Ala Ser Val Glu Glu Gly Asp Ala Asp Ala Asp Val Glu
             20                  25                  30

Ala Leu Arg Arg Leu Ser Asp Asn Leu Ala Ala Phe Arg Ser Pro
         35                  40                  45

Glu Asp Phe Ala Phe Leu Ala Asp Ala Arg Ile Ala Val Pro Gly Gly
 50                  55                  60

Gly Gly Gly Gly Gly Asp Leu Arg Val His Arg Cys Val Leu Ser Ala
 65                  70                  75                  80

Arg Ser Pro Phe Leu Arg Gly Val Phe Ala Arg Arg Ala Ala Ala
             85                  90                  95

Ala Gly Gly Gly Gly Glu Asp Gly Ser Glu Arg Leu Glu Leu Arg Glu
            100                 105                 110

Leu Leu Gly Gly Gly Gly Glu Glu Val Glu Val Gly Tyr Glu Ala Leu
            115                 120                 125

Arg Leu Val Leu Asp Tyr Leu Tyr Ser Gly Arg Val Gly Asp Leu Pro
        130                 135                 140

Lys Ala Ala Cys Leu Cys Val Asp Glu Asp Cys Ala His Val Gly Cys
145                 150                 155                 160

His Pro Ala Val Ala Phe Met Ala Gln Val Leu Phe Ala Ser Thr
                165                 170                 175

Phe Gln Val Ala Glu Leu Thr Asn Leu Phe Gln Arg Arg Leu Leu Asp
            180                 185                 190

Val Leu Asp Lys Val Glu Val Asp Asn Leu Leu Ile Leu Ser Val
        195                 200                 205

Ala Asn Leu Cys Asn Lys Ser Cys Met Lys Leu Leu Glu Arg Cys Leu
    210                 215                 220

Asp Met Val Val Arg Ser Asn Leu Asp Met Ile Thr Leu Glu Lys Ser
225                 230                 235                 240

Leu Pro Pro Asp Val Ile Lys Gln Ile Ile Asp Ala Arg Leu Ser Leu
                245                 250                 255

Gly Leu Ile Ser Pro Glu Asn Lys Gly Phe Pro Asn Lys His Val Arg
            260                 265                 270

Arg Ile His Arg Ala Leu Asp Ser Asp Val Glu Leu Val Arg Met
        275                 280                 285

Leu Leu Thr Glu Gly Gln Thr Asn Leu Asp Asp Ala Phe Ala Leu His
    290                 295                 300

Tyr Ala Val Glu His Cys Asp Ser Lys Ile Thr Thr Glu Leu Leu Asp
305                 310                 315                 320

Leu Ala Leu Ala Asp Val Asn His Arg Asn Pro Arg Gly Tyr Thr Val
```

```
                    325             330             335
Leu His Ile Ala Ala Arg Arg Arg Glu Pro Lys Ile Ile Val Ser Leu
            340                 345                 350

Leu Thr Lys Gly Ala Arg Pro Ala Asp Val Thr Phe Asp Gly Arg Lys
        355                 360                 365

Ala Val Gln Ile Ser Lys Arg Leu Thr Lys Gln Gly Asp Tyr Phe Gly
    370                 375                 380

Val Thr Glu Glu Gly Lys Pro Ser Pro Lys Asp Arg Leu Cys Ile Glu
385                 390                 395                 400

Ile Leu Glu Gln Ala Glu Arg Arg Asp Pro Gln Leu Gly Glu Ala Ser
                405                 410                 415

Val Ser Leu Ala Met Ala Gly Glu Ser Leu Arg Gly Arg Leu Leu Tyr
            420                 425                 430

Leu Glu Asn Arg Val Ala Leu Ala Arg Ile Met Phe Pro Met Glu Ala
        435                 440                 445

Arg Val Ala Met Asp Ile Ala Gln Val Asp Gly Thr Leu Glu Phe Asn
    450                 455                 460

Leu Gly Ser Gly Ala Asn Pro Pro Glu Arg Gln Arg Thr Thr Val
465                 470                 475                 480

Asp Leu Asn Glu Ser Pro Phe Ile Met Lys Glu His Leu Ala Arg
                485                 490                 495

Met Thr Ala Leu Ser Lys Thr Val Glu Leu Gly Lys Arg Phe Phe Pro
            500                 505                 510

Arg Cys Ser Asn Val Leu Asp Lys Ile Met Asp Glu Thr Asp Pro
        515                 520                 525

Val Ser Leu Gly Arg Asp Thr Ser Ala Glu Lys Arg Lys Arg Phe His
    530                 535                 540

Asp Leu Gln Asp Val Leu Gln Lys Ala Phe His Glu Asp Lys Glu Glu
545                 550                 555                 560

Asn Asp Arg Ser Gly Leu Ser Ser Ser Ser Ser Thr Ser Ile Gly
                565                 570                 575

Ala Ile Arg Pro Arg Arg
            580

<210> SEQ ID NO 5
<211> LENGTH: 949
<212> TYPE: DNA
<213> ORGANISM: Oryza sativa
<220> FEATURE:
<221> NAME/KEY: CDS
<222> LOCATION: (1)..(618)
<223> OTHER INFORMATION: NPR1 homologue 2 (NH2) protein that interacts
      with PNI protein

<400> SEQUENCE: 5 tac aat aca aag atg gag caa ggc caa gag tca aac aaa gac agg tta      48
Tyr Asn Thr Lys Met Glu Gln Gly Gln Glu Ser Asn Lys Asp Arg Leu
  1               5                  10                  15 tgt att gat ata tta gat agg gag atg ata agg aaa cct atg gca gtg     96
Cys Ile Asp Ile Leu Asp Arg Glu Met Ile Arg Lys Pro Met Ala Val
                 20                  25                  30 gaa gat tct gtc acc tcg cct ttg ttg gct gac gat ctt cac atg aag    144
Glu Asp Ser Val Thr Ser Pro Leu Leu Ala Asp Asp Leu His Met Lys
             35                  40                  45 ctt ctc tac ctt gaa aac aga gtt gca ttt gca aga tta ttt ttt cct    192
Leu Leu Tyr Leu Glu Asn Arg Val Ala Phe Ala Arg Leu Phe Phe Pro
         50                  55                  60
```

```
gca gaa gca aag gtt gca atg caa att gca caa gca gac acc aca cca      240
Ala Glu Ala Lys Val Ala Met Gln Ile Ala Gln Ala Asp Thr Thr Pro
 65                  70                  75                  80 gaa ttt ggc att gtt cct gca gct agc act tct gga aaa ttg aag gaa      288
Glu Phe Gly Ile Val Pro Ala Ala Ser Thr Ser Gly Lys Leu Lys Glu
                 85                  90                  95 gtc gat ctg aac gag aca cca gta aca caa aac aaa agg ctc cgt tca      336
Val Asp Leu Asn Glu Thr Pro Val Thr Gln Asn Lys Arg Leu Arg Ser
            100                 105                 110 agg gtg gat gca ctc atg aaa aca gtt gag ctg gga cgt cgc tac ttc      384
Arg Val Asp Ala Leu Met Lys Thr Val Glu Leu Gly Arg Arg Tyr Phe
        115                 120                 125 cct aac tgc tcg cag gtg ctc gac aaa ttt ctg gag gat gat ttg ccc      432
Pro Asn Cys Ser Gln Val Leu Asp Lys Phe Leu Glu Asp Asp Leu Pro
    130                 135                 140 gat agt cct gat gca ctc gac ctc caa aat ggc act tct gat gag caa      480
Asp Ser Pro Asp Ala Leu Asp Leu Gln Asn Gly Thr Ser Asp Glu Gln
145                 150                 155                 160 aat gtt aaa agg atg cgg ttc tgt gag tta aag gag gat gtg cgc aag      528
Asn Val Lys Arg Met Arg Phe Cys Glu Leu Lys Glu Asp Val Arg Lys
                165                 170                 175 gca ttc agc aaa gac aga gct gat aat agc atg ttt tct atc ttg tca      576
Ala Phe Ser Lys Asp Arg Ala Asp Asn Ser Met Phe Ser Ile Leu Ser
            180                 185                 190 tct tca tcg tcc tct tcg cca cct ccc aag gtt gca aag aaa              618
Ser Ser Ser Ser Ser Ser Pro Pro Pro Lys Val Ala Lys Lys
        195                 200                 205 tgacagaagt tttgtaacaa atttccgctc gtgatgttac tgggacaaga gatatcgatc    678
aatagacctg tatagtctta cagtggtata acaattagat atcgaagctt cttcgaatat    738
tagaaagtgc tgttctgggc tgcactcagc tggtttatgg gacccatgcg gtgaaactgg    798
caaaagaaaa ccagctgatt agaggctcca aagtagtgtc tctcgtgaat atgtttgtag    858
cattctgttt tgttcaggat ggctgtaatg ataaaatctt ttcaatagat atatagctaa    918
ttgtctcgta aaaaaaaaaa aaaaaaaaa a                                    949
```

<210> SEQ ID NO 6
<211> LENGTH: 206
<212> TYPE: PRT
<213> ORGANISM: Oryza sativa

<400> SEQUENCE: 6

```
Tyr Asn Thr Lys Met Glu Gln Gly Gln Glu Ser Asn Lys Asp Arg Leu
 1               5                  10                  15

Cys Ile Asp Ile Leu Asp Arg Glu Met Ile Arg Lys Pro Met Ala Val
             20                  25                  30

Glu Asp Ser Val Thr Ser Pro Leu Leu Ala Asp Asp Leu His Met Lys
         35                  40                  45

Leu Leu Tyr Leu Glu Asn Arg Val Ala Phe Ala Arg Leu Phe Phe Pro
     50                  55                  60

Ala Glu Ala Lys Val Ala Met Gln Ile Ala Gln Ala Asp Thr Thr Pro
 65                  70                  75                  80

Glu Phe Gly Ile Val Pro Ala Ala Ser Thr Ser Gly Lys Leu Lys Glu
                 85                  90                  95

Val Asp Leu Asn Glu Thr Pro Val Thr Gln Asn Lys Arg Leu Arg Ser
            100                 105                 110

Arg Val Asp Ala Leu Met Lys Thr Val Glu Leu Gly Arg Arg Tyr Phe
        115                 120                 125
```

```
Pro Asn Cys Ser Gln Val Leu Asp Lys Phe Leu Glu Asp Asp Leu Pro
        130                 135                 140

Asp Ser Pro Asp Ala Leu Asp Leu Gln Asn Gly Thr Ser Asp Glu Gln
145                 150                 155                 160

Asn Val Lys Arg Met Arg Phe Cys Glu Leu Lys Glu Asp Val Arg Lys
                165                 170                 175

Ala Phe Ser Lys Asp Arg Ala Asp Asn Ser Met Phe Ser Ile Leu Ser
                180                 185                 190

Ser Ser Ser Ser Ser Ser Pro Pro Pro Lys Val Ala Lys Lys
            195                 200                 205

<210> SEQ ID NO 7
<211> LENGTH: 602
<212> TYPE: DNA
<213> ORGANISM: Oryza sativa
<220> FEATURE:
<221> NAME/KEY: CDS
<222> LOCATION: (1)..(441)
<223> OTHER INFORMATION: nucleolin-like protein that interacts with PNI
      protein

<400> SEQUENCE: 7 gat gat aga gta cca cta cct agt tca aat gga gct cca ttg ctc ccg      48
Asp Asp Arg Val Pro Leu Pro Ser Ser Asn Gly Ala Pro Leu Leu Pro
 1               5                  10                  15 agt tat cct cca ctt gga tat ggt atc atg tca gta cca ggt gcc tat      96
Ser Tyr Pro Pro Leu Gly Tyr Gly Ile Met Ser Val Pro Gly Ala Tyr
                20                  25                  30 ggt gct gct cct gct agt act gca cag cct atg ctg tat gct cca aga     144
Gly Ala Ala Pro Ala Ser Thr Ala Gln Pro Met Leu Tyr Ala Pro Arg
            35                  40                  45 gct cct cca ggg gca gca atg gtt cca atg atg tta ccg gat ggt cat     192
Ala Pro Pro Gly Ala Ala Met Val Pro Met Met Leu Pro Asp Gly His
        50                  55                  60 ctc gta tat gtt gta caa cag cct ggt gga cag ttg ccg ctg gct tcg     240
Leu Val Tyr Val Val Gln Gln Pro Gly Gly Gln Leu Pro Leu Ala Ser
 65                  70                  75                  80 ccg ccg ccg cag caa gct gga cat cgt agc ggc agt gga gga cgt cat     288
Pro Pro Pro Gln Gln Ala Gly His Arg Ser Gly Ser Gly Gly Arg His
                85                  90                  95 ggc ggc agt ggc agc cgc tat ggc ggt ggt ggt ggc agc tcc ggc agt     336
Gly Gly Ser Gly Ser Arg Tyr Gly Gly Gly Gly Gly Ser Ser Gly Ser
            100                 105                 110 agc agg ccc ggt gca aaa cgg cag aga gga gat gac aac agc agt agc     384
Ser Arg Pro Gly Ala Lys Arg Gln Arg Gly Asp Asp Asn Ser Ser Ser
        115                 120                 125 cgc cac aaa ggc cgg cgc cgc cgt act gat ctg atc agc ata gct gta     432
Arg His Lys Gly Arg Arg Arg Thr Asp Leu Ile Ser Ile Ala Val
130                 135                 140 gct acc act tagaagatgt agtgccgtcg cagaaaatta ccagaaaatc              481
Ala Thr Thr
145 tggtagaaat aatttatact gtttgtactc atcgatttat tagaagaatt cgtttctgaa    541 acaagactgt acatgcgtat ttaccagtat tttccaatat cgcagaattg ctgaaaaaaa    601 a                                                                    602

<210> SEQ ID NO 8
<211> LENGTH: 147
<212> TYPE: PRT
```

<213> ORGANISM: Oryza sativa

<400> SEQUENCE: 8

```
Asp Asp Arg Val Pro Leu Pro Ser Ser Asn Gly Ala Pro Leu Leu Pro
  1               5                  10                  15

Ser Tyr Pro Pro Leu Gly Tyr Gly Ile Met Ser Val Pro Gly Ala Tyr
             20                  25                  30

Gly Ala Ala Pro Ala Ser Thr Ala Gln Pro Met Leu Tyr Ala Pro Arg
         35                  40                  45

Ala Pro Pro Gly Ala Ala Met Val Pro Met Met Leu Pro Asp Gly His
     50                  55                  60

Leu Val Tyr Val Val Gln Gln Pro Gly Gly Gln Leu Pro Leu Ala Ser
 65                  70                  75                  80

Pro Pro Pro Gln Gln Ala Gly His Arg Ser Gly Ser Gly Arg His
                 85                  90                  95

Gly Gly Ser Gly Ser Arg Tyr Gly Gly Gly Gly Ser Ser Gly Ser
             100                 105                 110

Ser Arg Pro Gly Ala Lys Arg Gln Arg Gly Asp Asp Asn Ser Ser Ser
         115                 120                 125

Arg His Lys Gly Arg Arg Arg Thr Asp Leu Ile Ser Ile Ala Val
     130                 135                 140

Ala Thr Thr
145
```

<210> SEQ ID NO 9
<211> LENGTH: 951
<212> TYPE: DNA
<213> ORGANISM: Oryza sativa
<220> FEATURE:
<221> NAME/KEY: CDS
<222> LOCATION: (1)..(792)
<223> OTHER INFORMATION: PREG-like protein that interacts with PNI protein

<400> SEQUENCE: 9

```
atg gac gcc gcc gcg gca gcg ggc ggc gag atg tcg cgg cag aag gcg        48
Met Asp Ala Ala Ala Ala Gly Gly Glu Met Ser Arg Gln Lys Ala
  1               5                  10                  15 acg gcg tcg gct ccg ccg ccg ccg gag ctg gac atg gtg gcg cgc gcc        96
Thr Ala Ser Ala Pro Pro Pro Pro Glu Leu Asp Met Val Ala Arg Ala
             20                  25                  30 gtg cag cgg ctg gtg gcg cgg aac gac gcg gtg gag gcg ctg agc ggc       144
Val Gln Arg Leu Val Ala Arg Asn Asp Ala Val Glu Ala Leu Ser Gly
         35                  40                  45 gga ggg gag gcg gcg gcg ggg cta gga gca ggg atg gcg gcg ttc gag       192
Gly Gly Glu Ala Ala Ala Gly Leu Gly Ala Gly Met Ala Ala Phe Glu
     50                  55                  60 gcg gcg agg ggc gcg ccg gcg ccg cgc atc ggc gtg gcg cag tat ctg       240
Ala Ala Arg Gly Ala Pro Ala Pro Arg Ile Gly Val Ala Gln Tyr Leu
 65                  70                  75                  80 gag cgc gtg cac cgg tac gcc ggg ctg gag ccg gag tgc tac gtg gtg       288
Glu Arg Val His Arg Tyr Ala Gly Leu Glu Pro Glu Cys Tyr Val Val
                 85                  90                  95 gcg tac gcg tac gtc gac atg gcg gcg cac cgc cgc ccc gcc gcc gcc       336
Ala Tyr Ala Tyr Val Asp Met Ala Ala His Arg Arg Pro Ala Ala Ala
             100                 105                 110 gtc gcc tcc cgc aac gtc cac cgc ctc ctc ctc gcc tgc ctc ctc gtc       384
Val Ala Ser Arg Asn Val His Arg Leu Leu Leu Ala Cys Leu Leu Val
         115                 120                 125
```

-continued

```
gcc tcc aag gtt ctc gac gac ttc cac cac aac aac gcg ttc ttc gcg      432
Ala Ser Lys Val Leu Asp Asp Phe His His Asn Asn Ala Phe Phe Ala
    130                 135                 140 cgc gtc ggc ggc gtg agc aac gcg gag atg aac agg ctg gag ctg gag      480
Arg Val Gly Gly Val Ser Asn Ala Glu Met Asn Arg Leu Glu Leu Glu
145                 150                 155                 160 ctc ctc gcc gtg ctg gac ttc gag gtc atg ctc agc cac cgc gtc tac      528
Leu Leu Ala Val Leu Asp Phe Glu Val Met Leu Ser His Arg Val Tyr
                165                 170                 175 gag ctc tac cac gag cac ctc aag aag gag gcg cgg agg gac ggc ggc      576
Glu Leu Tyr His Glu His Leu Lys Lys Glu Ala Arg Arg Asp Gly Gly
            180                 185                 190 gcc ggc gac atg ctc gcc ggc gcg tcg gcc gcc gcc gcc aag gcg          624
Ala Gly Asp Met Leu Ala Gly Ala Ser Ala Ala Ala Ala Lys Ala
        195                 200                 205 ggg aga atg gcg gcc gtc tcg ccg tcc aag ctg ctg gaa cgc gcg gcg      672
Gly Arg Met Ala Ala Val Ser Pro Ser Lys Leu Leu Glu Arg Ala Ala
210                 215                 220 gtg aac ggc gcc gcg cag cac gac gac tgg agg agc ctg ggt acg gcg      720
Val Asn Gly Ala Ala Gln His Asp Asp Trp Arg Ser Leu Gly Thr Ala
225                 230                 235                 240 gcg gcg gcg gag gcg gcg aac ggc gtg cgg cgg cac agg tcg tcg tcg      768
Ala Ala Ala Glu Ala Ala Asn Gly Val Arg Arg His Arg Ser Ser Ser
                245                 250                 255 tcg tcg cgg tat tcc ttc gat tgc tagtatagcc agcgttgcca aagagcgcgt    822
Ser Ser Arg Tyr Ser Phe Asp Cys
            260 tctgtgtgta tatatcaggt tatcaacgag agttttgag gctgtaaaaa aattaaagac    882 ggattaatta cctgccaaag tgccaattag caaatgtttc ccataaaaaa aaaaaaaaaa    942 aaaaaaaaa                                                             951

<210> SEQ ID NO 10
<211> LENGTH: 264
<212> TYPE: PRT
<213> ORGANISM: Oryza sativa

<400> SEQUENCE: 10

Met Asp Ala Ala Ala Ala Gly Gly Glu Met Ser Arg Gln Lys Ala
1               5                   10                  15

Thr Ala Ser Ala Pro Pro Pro Glu Leu Asp Met Val Ala Arg Ala
            20                  25                  30

Val Gln Arg Leu Val Ala Arg Asn Asp Ala Val Glu Ala Leu Ser Gly
        35                  40                  45

Gly Gly Glu Ala Ala Ala Gly Leu Gly Ala Gly Met Ala Ala Phe Glu
    50                  55                  60

Ala Ala Arg Gly Ala Pro Ala Pro Arg Ile Gly Val Ala Gln Tyr Leu
65                  70                  75                  80

Glu Arg Val His Arg Tyr Ala Gly Leu Glu Pro Glu Cys Tyr Val Val
                85                  90                  95

Ala Tyr Ala Tyr Val Asp Met Ala Ala His Arg Arg Pro Ala Ala Ala
            100                 105                 110

Val Ala Ser Arg Asn Val His Arg Leu Leu Leu Ala Cys Leu Leu Val
        115                 120                 125

Ala Ser Lys Val Leu Asp Asp Phe His His Asn Asn Ala Phe Phe Ala
    130                 135                 140

Arg Val Gly Gly Val Ser Asn Ala Glu Met Asn Arg Leu Glu Leu Glu
145                 150                 155                 160
```

-continued

```
Leu Leu Ala Val Leu Asp Phe Glu Val Met Leu Ser His Arg Val Tyr
            165                 170                 175

Glu Leu Tyr His Glu His Leu Lys Lys Glu Ala Arg Arg Asp Gly Gly
                180                 185                 190

Ala Gly Asp Met Leu Ala Gly Ala Ser Ala Ala Ala Ala Lys Ala
        195                 200                 205

Gly Arg Met Ala Ala Val Ser Pro Ser Lys Leu Leu Glu Arg Ala Ala
        210                 215                 220

Val Asn Gly Ala Ala Gln His Asp Asp Trp Arg Ser Leu Gly Thr Ala
225                 230                 235                 240

Ala Ala Ala Glu Ala Ala Asn Gly Val Arg Arg His Arg Ser Ser Ser
                245                 250                 255

Ser Ser Arg Tyr Ser Phe Asp Cys
            260
```

<210> SEQ ID NO 11
<211> LENGTH: 621
<212> TYPE: DNA
<213> ORGANISM: Oryza sativa
<220> FEATURE:
<221> NAME/KEY: CDS
<222> LOCATION: (1)..(621)
<223> OTHER INFORMATION: novel protein that interacts with PNI protein

<400> SEQUENCE: 11

```
agt gct agt gat gaa gcc ctt gca aaa gca gca tct ctg tat gga ggt      48
Ser Ala Ser Asp Glu Ala Leu Ala Lys Ala Ala Ser Leu Tyr Gly Gly
 1               5                  10                  15 gct cta aga aat gtt gag aaa gag tac gaa gaa ttt aat aga att tta      96
Ala Leu Arg Asn Val Glu Lys Glu Tyr Glu Glu Phe Asn Arg Ile Leu
                20                  25                  30 tct tct cag act ata gat cca ttg agg gct atg gct gca ggc gct ccc     144
Ser Ser Gln Thr Ile Asp Pro Leu Arg Ala Met Ala Ala Gly Ala Pro
            35                  40                  45 ctg gaa gat gct cgt ggt ctt gca caa cgt tat agc cgg atg aga cat     192
Leu Glu Asp Ala Arg Gly Leu Ala Gln Arg Tyr Ser Arg Met Arg His
        50                  55                  60 gaa gct gag atc ctt tct gct gaa att gct aga agg aag caa cgg gta     240
Glu Ala Glu Ile Leu Ser Ala Glu Ile Ala Arg Arg Lys Gln Arg Val
 65                  70                  75                  80 cga gaa gct cca gtt gct gag cac act acg aag ctt caa cag tct gaa     288
Arg Glu Ala Pro Val Ala Glu His Thr Thr Lys Leu Gln Gln Ser Glu
                 85                  90                  95 tct aaa atg ata gag cac aaa gca agc atg gct gtg tta gga aag gaa     336
Ser Lys Met Ile Glu His Lys Ala Ser Met Ala Val Leu Gly Lys Glu
            100                 105                 110 gct gct gct gca ctt gcc gct gtt gaa tct cag cag caa agg ata act     384
Ala Ala Ala Ala Leu Ala Ala Val Glu Ser Gln Gln Gln Arg Ile Thr
        115                 120                 125 ctt cag cgc ctg gtt ggc atg gta gaa gca gaa aag tta ttt cat ttg     432
Leu Gln Arg Leu Val Gly Met Val Glu Ala Glu Lys Leu Phe His Leu
    130                 135                 140 agg tta gct gct ata ctt gat gat gtt gaa gct gag atg tcc tct gaa     480
Arg Leu Ala Ala Ile Leu Asp Asp Val Glu Ala Glu Met Ser Ser Glu
145                 150                 155                 160 aag caa aag aga gaa tct gca ccg cct act att cat tct cat aag cgt     528
Lys Gln Lys Arg Glu Ser Ala Pro Pro Thr Ile His Ser His Lys Arg
                165                 170                 175 gct gag aag gcc cag tac ttc ctt gct gag gcg gtg cat aac ttc aat     576
Ala Glu Lys Ala Gln Tyr Phe Leu Ala Glu Ala Val His Asn Phe Asn
```

```
Ala Glu Lys Ala Gln Tyr Phe Leu Ala Glu Ala Val His Asn Phe Asn
            180                 185                 190 ggt acc aca gaa aag gag ttg agt tta att gtg gtg att atg tcg          621
Gly Thr Thr Glu Lys Glu Leu Ser Leu Ile Val Val Ile Met Ser
            195                 200                 205

<210> SEQ ID NO 12
<211> LENGTH: 207
<212> TYPE: PRT
<213> ORGANISM: Oryza sativa

<400> SEQUENCE: 12

Ser Ala Ser Asp Glu Ala Leu Ala Lys Ala Ala Ser Leu Tyr Gly Gly
  1               5                  10                  15

Ala Leu Arg Asn Val Glu Lys Glu Tyr Glu Glu Phe Asn Arg Ile Leu
             20                  25                  30

Ser Ser Gln Thr Ile Asp Pro Leu Arg Ala Met Ala Ala Gly Ala Pro
         35                  40                  45

Leu Glu Asp Ala Arg Gly Leu Ala Gln Arg Tyr Ser Arg Met Arg His
     50                  55                  60

Glu Ala Glu Ile Leu Ser Ala Glu Ile Ala Arg Arg Lys Gln Arg Val
 65                  70                  75                  80

Arg Glu Ala Pro Val Ala Glu His Thr Thr Lys Leu Gln Gln Ser Glu
                 85                  90                  95

Ser Lys Met Ile Glu His Lys Ala Ser Met Ala Val Leu Gly Lys Glu
            100                 105                 110

Ala Ala Ala Ala Leu Ala Ala Val Glu Ser Gln Gln Gln Arg Ile Thr
        115                 120                 125

Leu Gln Arg Leu Val Gly Met Val Glu Ala Glu Lys Leu Phe His Leu
    130                 135                 140

Arg Leu Ala Ala Ile Leu Asp Asp Val Glu Ala Glu Met Ser Ser Glu
145                 150                 155                 160

Lys Gln Lys Arg Glu Ser Ala Pro Pro Thr Ile His Ser His Lys Arg
                165                 170                 175

Ala Glu Lys Ala Gln Tyr Phe Leu Ala Glu Ala Val His Asn Phe Asn
            180                 185                 190

Gly Thr Thr Glu Lys Glu Leu Ser Leu Ile Val Val Ile Met Ser
            195                 200                 205

<210> SEQ ID NO 13
<211> LENGTH: 444
<212> TYPE: DNA
<213> ORGANISM: Oryza sativa
<220> FEATURE:
<221> NAME/KEY: CDS
<222> LOCATION: (1)..(441)
<223> OTHER INFORMATION: GRL1 homologue of glutaredoxin that interacts
      with MN1

<400> SEQUENCE: 13 atg tac cag gcg atc ccg tac agc agc acc cgg ccg tgg ctc agg ccg           48
Met Tyr Gln Ala Ile Pro Tyr Ser Ser Thr Arg Pro Trp Leu Arg Pro
  1               5                  10                  15 gag ccg gcg gcg agc gtg gtc gac gtc gtg aag gtg gag acg acg acg           96
Glu Pro Ala Ala Ser Val Val Asp Val Val Lys Val Glu Thr Thr Thr
             20                  25                  30 gcc gtc gcg ggt cgg ggc ggt gag gcg gag gtc gtg ggg gag gag gag          144
Ala Val Ala Gly Arg Gly Gly Glu Ala Glu Val Val Gly Glu Glu Glu
         35                  40                  45
```

```
gcg gcg gag gtg cgg agg gcg gtg gcg gag agc ccg gtg ctg gtg gtg         192
Ala Ala Glu Val Arg Arg Ala Val Ala Glu Ser Pro Val Leu Val Val
 50                  55                  60 ggg agg cgc ggg tgc tgc ctc atc cac gtg gtg aag cgg ctg ctg cag         240
Gly Arg Arg Gly Cys Cys Leu Ile His Val Val Lys Arg Leu Leu Gln
 65                  70                  75                  80 ggg ctc ggg gtc aac ccg gcc gtg cac gag gtc gcc ggc gag gcc gcg         288
Gly Leu Gly Val Asn Pro Ala Val His Glu Val Ala Gly Glu Ala Ala
                 85                  90                  95 ctc aag ggg gtt gtg ccg gcc ggt ggg gag gcc gcg gcg ctc ccc gcc         336
Leu Lys Gly Val Val Pro Ala Gly Gly Glu Ala Ala Ala Leu Pro Ala
            100                 105                 110 gtg ttc gtc ggg ggg aag ctc ctc ggc ggg ctc gac gcc ctc atg gcc         384
Val Phe Val Gly Gly Lys Leu Leu Gly Gly Leu Asp Arg Leu Met Ala
        115                 120                 125 gtc cac atc tcc ggc gag ctc gtg ccc atc ctc aag aag gcc ggt gcc         432
Val His Ile Ser Gly Glu Leu Val Pro Ile Leu Lys Lys Ala Gly Ala
130                 135                 140 ctc tgg ctt taa                                                         444
Leu Trp Leu
145
```

<210> SEQ ID NO 14
<211> LENGTH: 147
<212> TYPE: PRT
<213> ORGANISM: Oryza sativa

<400> SEQUENCE: 14

```
Met Tyr Gln Ala Ile Pro Tyr Ser Ser Thr Arg Pro Trp Leu Arg Pro
 1               5                   10                  15

Glu Pro Ala Ala Ser Val Val Asp Val Val Lys Val Glu Thr Thr Thr
             20                  25                  30

Ala Val Ala Gly Arg Gly Gly Glu Ala Glu Val Val Gly Glu Glu Glu
         35                  40                  45

Ala Ala Glu Val Arg Arg Ala Val Ala Glu Ser Pro Val Leu Val Val
 50                  55                  60

Gly Arg Arg Gly Cys Cys Leu Ile His Val Val Lys Arg Leu Leu Gln
 65                  70                  75                  80

Gly Leu Gly Val Asn Pro Ala Val His Glu Val Ala Gly Glu Ala Ala
                 85                  90                  95

Leu Lys Gly Val Val Pro Ala Gly Gly Glu Ala Ala Ala Leu Pro Ala
            100                 105                 110

Val Phe Val Gly Gly Lys Leu Leu Gly Gly Leu Asp Arg Leu Met Ala
        115                 120                 125

Val His Ile Ser Gly Glu Leu Val Pro Ile Leu Lys Lys Ala Gly Ala
130                 135                 140

Leu Trp Leu
145
```

<210> SEQ ID NO 15
<211> LENGTH: 393
<212> TYPE: DNA
<213> ORGANISM: Oryza sativa
<220> FEATURE:
<221> NAME/KEY: CDS
<222> LOCATION: (1)..(390)
<223> OTHER INFORMATION: GRL2 homologue of glutaredoxin that interacts
      with MN1

<400> SEQUENCE: 15

-continued

```
atg tac cag gcg atc ccg tac aac gcg aac cgg gct tgg ccg gcg gcg        48
Met Tyr Gln Ala Ile Pro Tyr Asn Ala Asn Arg Ala Trp Pro Ala Ala
1               5                   10                  15 agc cgg ccg gcg acg gcg ccg ccg ccg ccg ccg cgt gga gag                 96
Ser Arg Pro Ala Thr Ala Pro Pro Pro Pro Pro Arg Gly Glu
            20                  25                  30 gag gag gag gtg agg agg gcg gtg gcg gag tgc ccg gtg gtg gtg gtg        144
Glu Glu Glu Val Arg Arg Ala Val Ala Glu Cys Pro Val Val Val Val
        35                  40                  45 ggt cgg agc ggg tgc tgc ctg agc cac gtc gtg aag cgg ctg ctg cag        192
Gly Arg Ser Gly Cys Cys Leu Ser His Val Val Lys Arg Leu Leu Gln
50                  55                  60 ggg ctc ggg gtc aac ccg gcg gtg cac gag gtc gcc ggc gag gcc gag        240
Gly Leu Gly Val Asn Pro Ala Val His Glu Val Ala Gly Glu Ala Glu
65                  70                  75                  80 ctc gcc ggg gtg gtc gcc ggc ggc ggc gtc gcg ctg ccg gcg gtg            288
Leu Ala Gly Val Val Ala Gly Gly Gly Val Ala Leu Pro Ala Val
                85                  90                  95 ttc gtc ggc ggg agg ctc ctc ggc ggg ctc gac cgg ctc atg gcc gtg        336
Phe Val Gly Gly Arg Leu Leu Gly Gly Leu Asp Arg Leu Met Ala Val
            100                 105                 110 cac atc tcc ggc gag ctc gtg ccc att ctg aag gag gcc ggt gca ctc        384
His Ile Ser Gly Glu Leu Val Pro Ile Leu Lys Glu Ala Gly Ala Leu
        115                 120                 125 tgg ctc tga                                                            393
Trp Leu
130
```

<210> SEQ ID NO 16
<211> LENGTH: 130
<212> TYPE: PRT
<213> ORGANISM: Oryza sativa

<400> SEQUENCE: 16

```
Met Tyr Gln Ala Ile Pro Tyr Asn Ala Asn Arg Ala Trp Pro Ala Ala
1               5                   10                  15

Ser Arg Pro Ala Thr Ala Pro Pro Pro Pro Pro Arg Gly Glu
            20                  25                  30

Glu Glu Glu Val Arg Arg Ala Val Ala Glu Cys Pro Val Val Val Val
        35                  40                  45

Gly Arg Ser Gly Cys Cys Leu Ser His Val Val Lys Arg Leu Leu Gln
50                  55                  60

Gly Leu Gly Val Asn Pro Ala Val His Glu Val Ala Gly Glu Ala Glu
65                  70                  75                  80

Leu Ala Gly Val Val Ala Gly Gly Gly Val Ala Leu Pro Ala Val
                85                  90                  95

Phe Val Gly Gly Arg Leu Leu Gly Gly Leu Asp Arg Leu Met Ala Val
            100                 105                 110

His Ile Ser Gly Glu Leu Val Pro Ile Leu Lys Glu Ala Gly Ala Leu
        115                 120                 125

Trp Leu
130
```

<210> SEQ ID NO 17
<211> LENGTH: 651
<212> TYPE: DNA
<213> ORGANISM: Oryza sativa
<220> FEATURE:
<221> NAME/KEY: CDS
<222> LOCATION: (1)..(651)

<223> OTHER INFORMATION: protein homologue to rat microtubule-associated
      protein 1A (MAP1A) that interacts with MN1

<400> SEQUENCE: 17

```
atg ggc tcg tcg gcg gcc gac tcg ttc ccc gcc ggt gga gat gat gca        48
Met Gly Ser Ser Ala Ala Asp Ser Phe Pro Ala Gly Gly Asp Asp Ala
1               5                   10                  15 atc cga gac gtg tac ggc atc ggt ggt ggt ggg gag gag gac gat ccg        96
Ile Arg Asp Val Tyr Gly Ile Gly Gly Gly Gly Glu Glu Asp Asp Pro
                20                  25                  30 tcc ctc ttc ctc tac ctc tcc gac ctc gcc ccc gtc tcc ccc tcc gcc       144
Ser Leu Phe Leu Tyr Leu Ser Asp Leu Ala Pro Val Ser Pro Ser Ala
            35                  40                  45 tac ctc gac ctc ccc ccc tcg ccg ccg ccg acg acg acg gct acg            192
Tyr Leu Asp Leu Pro Pro Ser Pro Pro Pro Thr Thr Thr Ala Thr
        50                  55                  60 acg atg gtg aag gag ggg gag gag gcg ccg gag gac ctg gtg ctg ccg       240
Thr Met Val Lys Glu Gly Glu Glu Ala Pro Glu Asp Leu Val Leu Pro
65                  70                  75                  80 ttc atc tcg agg atg ctg atc gag gag gac atc gac gac aag ttc ttc      288
Phe Ile Ser Arg Met Leu Ile Glu Glu Asp Ile Asp Asp Lys Phe Phe
                85                  90                  95 tac gac tac ccc gac aac ccg gcg ctg ctc cag gcg cag cag ccc ttc      336
Tyr Asp Tyr Pro Asp Asn Pro Ala Leu Leu Gln Ala Gln Gln Pro Phe
                100                 105                 110 ctc gag atc ctc tcc gat ccc tcc tcc aac tcc cgc tcc tcc aac tcc      384
Leu Glu Ile Leu Ser Asp Pro Ser Ser Asn Ser Arg Ser Ser Asn Ser
            115                 120                 125 gac gac ccc cgc ctc tcc ccg acc tcc tcc tcc gac acc tcc gcc gcc      432
Asp Asp Pro Arg Leu Ser Pro Thr Ser Ser Ser Asp Thr Ser Ala Ala
130                 135                 140 atc aac tcc tac gac gcc gcc gcc acc gcc acc gcc gtt gcc gcc gcc      480
Ile Asn Ser Tyr Asp Ala Ala Ala Thr Ala Thr Ala Val Ala Ala Ala
145                 150                 155                 160 gcg gtg ccc gtg ccg cag tac gag agc atc gag ctc gat ccc gcc gcg      528
Ala Val Pro Val Pro Gln Tyr Glu Ser Ile Glu Leu Asp Pro Ala Ala
                165                 170                 175 ttc ttc gcc gcg gcc aac tcc gac ctc atg agc tcc gct tct caa ggg      576
Phe Phe Ala Ala Ala Asn Ser Asp Leu Met Ser Ser Ala Ser Gln Gly
                180                 185                 190 gat gga gga ggc gaa caa gtt cct ccc acc gag aac aag ctc gtc atc      624
Asp Gly Gly Gly Glu Gln Val Pro Pro Thr Glu Asn Lys Leu Val Ile
            195                 200                 205 gac ctc gag gcc tcg tcg gag aat aat                                   651
Asp Leu Glu Ala Ser Ser Glu Asn Asn
        210                 215
```

<210> SEQ ID NO 18
<211> LENGTH: 217
<212> TYPE: PRT
<213> ORGANISM: Oryza sativa

<400> SEQUENCE: 18

```
Met Gly Ser Ser Ala Ala Asp Ser Phe Pro Ala Gly Gly Asp Asp Ala
1               5                   10                  15

Ile Arg Asp Val Tyr Gly Ile Gly Gly Gly Gly Glu Glu Asp Asp Pro
                20                  25                  30

Ser Leu Phe Leu Tyr Leu Ser Asp Leu Ala Pro Val Ser Pro Ser Ala
            35                  40                  45

Tyr Leu Asp Leu Pro Pro Ser Pro Pro Pro Thr Thr Thr Ala Thr
```

-continued

```
                 50                  55                  60
Thr Met Val Lys Glu Gly Glu Ala Pro Glu Asp Leu Val Leu Pro
 65                  70                  75                  80

Phe Ile Ser Arg Met Leu Ile Glu Glu Asp Ile Asp Lys Phe Phe
                 85                  90                  95

Tyr Asp Tyr Pro Asp Asn Pro Ala Leu Leu Gln Ala Gln Pro Phe
                100                 105                 110

Leu Glu Ile Leu Ser Asp Pro Ser Asn Ser Arg Ser Ser Asn Ser
            115                 120                 125

Asp Asp Pro Arg Leu Ser Pro Thr Ser Ser Asp Thr Ser Ala Ala
130                 135                 140

Ile Asn Ser Tyr Asp Ala Ala Thr Ala Thr Ala Val Ala Ala Ala
145                 150                 155                 160

Ala Val Pro Val Pro Gln Tyr Glu Ser Ile Glu Leu Asp Pro Ala Ala
                165                 170                 175

Phe Phe Ala Ala Ala Asn Ser Asp Leu Met Ser Ser Ala Ser Gln Gly
                180                 185                 190

Asp Gly Gly Glu Gln Val Pro Pro Thr Glu Asn Lys Leu Val Ile
            195                 200                 205

Asp Leu Glu Ala Ser Ser Glu Asn Asn
    210                 215

<210> SEQ ID NO 19
<211> LENGTH: 1005
<212> TYPE: DNA
<213> ORGANISM: Oryza sativa
<220> FEATURE:
<223> OTHER INFORMATION: rice bZIP protein MN1 cDNA
<221> NAME/KEY: CDS
<222> LOCATION: (1)..(1002)

<400> SEQUENCE: 19 atg gca gat gct agt tca agg act gac aca tcg att gtt gta gac aac      48
Met Ala Asp Ala Ser Ser Arg Thr Asp Thr Ser Ile Val Val Asp Asn
  1               5                  10                  15 gac gac aaa aac cac cag tta gaa aac gga cat agt ggt gca gtc atg      96
Asp Asp Lys Asn His Gln Leu Glu Asn Gly His Ser Gly Ala Val Met
             20                  25                  30 gct tct aac tct tca gat aga tct gac aga tct gac aaa ctt atg gac     144
Ala Ser Asn Ser Ser Asp Arg Ser Asp Arg Ser Asp Lys Leu Met Asp
         35                  40                  45 caa aag aca atg cgg cgg ctt gct caa aat cgt gag gca gca aga aaa     192
Gln Lys Thr Met Arg Arg Leu Ala Gln Asn Arg Glu Ala Ala Arg Lys
     50                  55                  60 agt cgg ctg agg aaa aag gca tat gtg caa caa cta gag agc agt aag     240
Ser Arg Leu Arg Lys Lys Ala Tyr Val Gln Gln Leu Glu Ser Ser Lys
 65                  70                  75                  80 ctg aag ctt gca cag cta gag cag gaa ctt cag aaa gct cgt cag cag     288
Leu Lys Leu Ala Gln Leu Glu Gln Glu Leu Gln Lys Ala Arg Gln Gln
                 85                  90                  95 gga atc ttc atc tct agc tct gga gac cag acc cat gcc atg agt gga     336
Gly Ile Phe Ile Ser Ser Ser Gly Asp Gln Thr His Ala Met Ser Gly
            100                 105                 110 aat ggg gca ttg act ttt gac tta gaa tac act aga tgg ctc gag gag     384
Asn Gly Ala Leu Thr Phe Asp Leu Glu Tyr Thr Arg Trp Leu Glu Glu
        115                 120                 125 caa aat aag cag ata aat gag ttg agg aca gca gtg aat gct cat gca     432
Gln Asn Lys Gln Ile Asn Glu Leu Arg Thr Ala Val Asn Ala His Ala
    130                 135                 140
```

```
agt gac agt gac ctt cgt ctt att gtt gat ggc ata atg gcg cat tat    480
Ser Asp Ser Asp Leu Arg Leu Ile Val Asp Gly Ile Met Ala His Tyr
145                 150                 155                 160 gac gag gta ttc aag gtt aag ggt gta gct gca aag gcc gat gtg ttt    528
Asp Glu Val Phe Lys Val Lys Gly Val Ala Ala Lys Ala Asp Val Phe
                165                 170                 175 cat ata ctt tca ggc atg tgg aag aca ccc gca gaa aga tgc ttc ctg    576
His Ile Leu Ser Gly Met Trp Lys Thr Pro Ala Glu Arg Cys Phe Leu
            180                 185                 190 tgg ctt ggt ggt ttc cgt cca tct gag ctt cta aag ctc cta gca aat    624
Trp Leu Gly Gly Phe Arg Pro Ser Glu Leu Leu Lys Leu Leu Ala Asn
        195                 200                 205 cac ctc gaa cct tta acc gag cag cag ttg ctg gga tta aac aac ctc    672
His Leu Glu Pro Leu Thr Glu Gln Gln Leu Leu Gly Leu Asn Asn Leu
    210                 215                 220 cag gaa tct tct cag cag gcg gag gat gca ctt tca caa ggt atg gaa    720
Gln Glu Ser Ser Gln Gln Ala Glu Asp Ala Leu Ser Gln Gly Met Glu
225                 230                 235                 240 gca ctg cag caa tct ctg gca gat act ttg gct gga tct ctc gct tca    768
Ala Leu Gln Gln Ser Leu Ala Asp Thr Leu Ala Gly Ser Leu Ala Ser
                245                 250                 255 tca ggg tct tct ggg aat gtg gcg aac tac atg ggt cag atg gca atg    816
Ser Gly Ser Ser Gly Asn Val Ala Asn Tyr Met Gly Gln Met Ala Met
            260                 265                 270 gcc atg ggt aaa cta gga acg ctc gag aat ttc ctt tgc cag gcg gac    864
Ala Met Gly Lys Leu Gly Thr Leu Glu Asn Phe Leu Cys Gln Ala Asp
        275                 280                 285 aac ctg cga cag cag aca ttg cat caa atg caa cga att ctg acg atc    912
Asn Leu Arg Gln Gln Thr Leu His Gln Met Gln Arg Ile Leu Thr Ile
    290                 295                 300 cgg caa gcc tcg cgt gct ctt ctt gcc ata cac gat tac ttt tca cgc    960
Arg Gln Ala Ser Arg Ala Leu Leu Ala Ile His Asp Tyr Phe Ser Arg
305                 310                 315                 320 ttg cgt gct ttg agt tcg ctg tgg ctt gct agg cca cgg gag taa        1005
Leu Arg Ala Leu Ser Ser Leu Trp Leu Ala Arg Pro Arg Glu
                325                 330
```

<210> SEQ ID NO 20
<211> LENGTH: 334
<212> TYPE: PRT
<213> ORGANISM: Oryza sativa
<220>
<223> OTHER INFORMATION: rice bZIP protein MN1 cDNA

<400> SEQUENCE: 20

```
Met Ala Asp Ala Ser Ser Arg Thr Asp Thr Ser Ile Val Val Asp Asn
1               5                   10                  15

Asp Asp Lys Asn His Gln Leu Glu Asn Gly His Ser Gly Ala Val Met
            20                  25                  30

Ala Ser Asn Ser Ser Asp Arg Ser Asp Arg Ser Asp Lys Leu Met Asp
        35                  40                  45

Gln Lys Thr Met Arg Arg Leu Ala Gln Asn Arg Glu Ala Ala Arg Lys
    50                  55                  60

Ser Arg Leu Arg Lys Lys Ala Tyr Val Gln Gln Leu Glu Ser Ser Lys
65                  70                  75                  80

Leu Lys Leu Ala Gln Leu Glu Gln Glu Leu Gln Lys Ala Arg Gln Gln
                85                  90                  95

Gly Ile Phe Ile Ser Ser Ser Gly Asp Gln Thr His Ala Met Ser Gly
            100                 105                 110
```

Asn Gly Ala Leu Thr Phe Asp Leu Glu Tyr Thr Arg Trp Leu Glu Glu
            115                 120                 125

Gln Asn Lys Gln Ile Asn Glu Leu Arg Thr Ala Val Asn Ala His Ala
        130                 135                 140

Ser Asp Ser Asp Leu Arg Leu Ile Val Asp Gly Ile Met Ala His Tyr
145                 150                 155                 160

Asp Glu Val Phe Lys Val Lys Gly Val Ala Ala Lys Ala Asp Val Phe
                165                 170                 175

His Ile Leu Ser Gly Met Trp Lys Thr Pro Ala Glu Arg Cys Phe Leu
            180                 185                 190

Trp Leu Gly Gly Phe Arg Pro Ser Glu Leu Leu Lys Leu Leu Ala Asn
        195                 200                 205

His Leu Glu Pro Leu Thr Glu Gln Gln Leu Leu Gly Leu Asn Asn Leu
    210                 215                 220

Gln Glu Ser Ser Gln Gln Ala Glu Asp Ala Leu Ser Gln Gly Met Glu
225                 230                 235                 240

Ala Leu Gln Gln Ser Leu Ala Asp Thr Leu Ala Gly Ser Leu Ala Ser
                245                 250                 255

Ser Gly Ser Ser Gly Asn Val Ala Asn Tyr Met Gly Gln Met Ala Met
            260                 265                 270

Ala Met Gly Lys Leu Gly Thr Leu Glu Asn Phe Leu Cys Gln Ala Asp
        275                 280                 285

Asn Leu Arg Gln Gln Thr Leu His Gln Met Gln Arg Ile Leu Thr Ile
    290                 295                 300

Arg Gln Ala Ser Arg Ala Leu Leu Ala Ile His Asp Tyr Phe Ser Arg
305                 310                 315                 320

Leu Arg Ala Leu Ser Ser Leu Trp Leu Ala Arg Pro Arg Glu
                325                 330

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:anchor
      primer SS20

<400> SEQUENCE: 21
agggatgttt aataccacta c                                            21

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:
      gene-specific primer mn1-1

<400> SEQUENCE: 22
gaagccatga ctgcacca                                                18

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:
      gene-specific primer mn8-1

<400> SEQUENCE: 23

-continued

```
ttatcgtcgg tatccagga                                             19

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:anchor
      primer ADR1

<400> SEQUENCE: 24
acccgggaga gatcgaattc ggcacga                                    27

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence:
      gene-specific primer mn1-2

<400> SEQUENCE: 25
caccactatg tccgttttc                                             19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence:
      gene-specific primer mn8-2

<400> SEQUENCE: 26
ggactgttga tgtgtcagt                                             19
```